United States Patent
Perni et al.

(10) Patent No.: US 8,247,532 B2
(45) Date of Patent: *Aug. 21, 2012

(54) DEUTERATED HEPATITIS C PROTEASE INHIBITORS

(75) Inventors: Robert B. Perni, Marlborough, MA (US); Youssef Bennani, Boston, MA (US); Gregor Zlokarnik, La Jolla, CA (US); Gerald J. Tanoury, Hudson, MA (US); Minzhang Chen, Acton, MA (US); Young Chun Jung, Lexington, MA (US); Raymond E. Forslund, Natick, MA (US); Francois Maltais, Tewksbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/953,876

(22) Filed: Nov. 24, 2010

(65) Prior Publication Data

US 2011/0071074 A1  Mar. 24, 2011

Related U.S. Application Data

(63) Continuation of application No. 11/717,991, filed on Mar. 14, 2007, now abandoned.

(60) Provisional application No. 60/844,771, filed on Sep. 15, 2006, provisional application No. 60/782,976, filed on Mar. 16, 2006, provisional application No. 60/782,788, filed on Mar. 16, 2006.

(51) Int. Cl.
 *A61K 38/04* (2006.01)
(52) U.S. Cl. ...................................................... 530/330
(58) Field of Classification Search .................... 530/330
 See application file for complete search history.

(56) References Cited

U.S. PATENT DOCUMENTS

| | | | |
|---|---|---|---|
| 4,499,082 A | 2/1985 | Shenvi et al. |
| 4,720,484 A | 1/1988 | Vincent et al. |
| 4,880,780 A | 11/1989 | Trainor et al. |
| 5,053,519 A | 10/1991 | Teetz et al. |
| 5,231,084 A | 7/1993 | Hock et al. |
| 5,371,072 A | 12/1994 | Webb et al. |
| 5,384,410 A | 1/1995 | Kettner |
| 5,468,858 A | 11/1995 | Berlin et al. |
| 5,484,801 A | 1/1996 | Al-Razzak et al. |
| 5,496,927 A | 3/1996 | Kolb et al. |
| 5,502,061 A | 3/1996 | Hui et al. |
| 5,559,158 A | 9/1996 | Al-Razzak et al. |
| 5,610,193 A | 3/1997 | Al-Razzak et al. |
| 5,656,600 A | 8/1997 | Abelman et al. |
| 5,656,627 A | 8/1997 | Bemis et al. |
| 5,672,582 A | 9/1997 | Veber et al. |
| 5,716,929 A | 2/1998 | Bemis et al. |
| 5,725,878 A | 3/1998 | Al-Razzak et al. |
| 5,736,520 A | 4/1998 | Bey et al. |
| 5,756,466 A | 5/1998 | Bemis et al. |
| 5,760,029 A | 6/1998 | Jadhav et al. |
| 5,807,876 A | 9/1998 | Armistead et al. |
| 5,847,135 A | 12/1998 | Bemis et al. |
| 5,849,866 A | 12/1998 | Kolb |
| 5,861,267 A | 1/1999 | Su |
| 5,866,684 A | 2/1999 | Attwood et al. |
| 5,948,436 A | 9/1999 | Al-Razzak et al. |
| 5,973,111 A | 10/1999 | Bemis et al. |
| 5,990,276 A | 11/1999 | Zhang et al. |
| 6,018,020 A | 1/2000 | Attwood et al. |
| 6,025,147 A | 2/2000 | Bemis et al. |
| 6,025,516 A | 2/2000 | Ramaswamy et al. |
| 6,037,157 A | 3/2000 | Norbeck |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bemis et al. |
| 6,117,639 A | 9/2000 | Germann et al. |
| 6,130,315 A | 10/2000 | Kolb |
| 6,143,715 A | 11/2000 | Llinas-Brunet et al. |
| 6,153,579 A | 11/2000 | Kim et al. |
| 6,172,077 B1 | 1/2001 | Curtis et al. |
| 6,183,121 B1 | 2/2001 | Kim et al. |
| 6,211,338 B1 | 4/2001 | Malcolm et al. |
| 6,221,335 B1 * | 4/2001 | Foster .......................... 424/1.81 |
| 6,225,320 B1 | 5/2001 | Kulagowski et al. |
| 6,251,583 B1 | 6/2001 | Zhang et al. |

(Continued)

FOREIGN PATENT DOCUMENTS

DE  3211676  10/1983

(Continued)

OTHER PUBLICATIONS

Dyck, Journal of Neurochemistry vol. 46 Issue 2, pp. 399-404 (1986).*

(Continued)

*Primary Examiner* — James O Wilson
*Assistant Examiner* — Brian McDowell
(74) *Attorney, Agent, or Firm* — Honigman Miller Schwartz and Cohn; Kathryn D. Soulier; Jonathan P. O'Brien

(57) ABSTRACT

This invention relates to processes and intermediates for the preparation of salts of deuterated, enantiomerically enriched alpha-amino beta-hydroxy acids of Formula 1

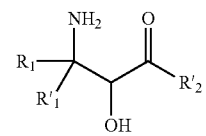

wherein the variables $R_1$, $R'_1$ and $R'_2$ are defined herein, and wherein the process may comprise the steps of forming a salt of a compound of Formula 1, and crystallizing said salt to give a compound of greater than 55% enantiomeric excess.

20 Claims, No Drawings

U.S. PATENT DOCUMENTS

| | | |
|---|---|---|
| 6,265,380 B1 | 7/2001 | Tung et al. |
| 6,268,207 B1 | 7/2001 | Bailey et al. |
| 6,274,613 B1 | 8/2001 | Plant et al. |
| 6,303,287 B1 | 10/2001 | Kim et al. |
| 6,323,180 B1 | 11/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Shi |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet et al. |
| 6,420,522 B1 | 7/2002 | Bemis et al. |
| 6,440,710 B1 * | 8/2002 | Keinan et al. ............... 435/148 |
| 6,498,178 B2 | 12/2002 | Stamos et al. |
| 6,528,276 B1 | 3/2003 | Germann et al. |
| 6,534,523 B1 | 3/2003 | Llinas-Brunet et al. |
| 6,541,496 B1 | 4/2003 | Armistead et al. |
| 6,548,555 B1 | 4/2003 | Curatolo et al. |
| 6,603,008 B1 * | 8/2003 | Ando et al. ............... 546/269.7 |
| 6,608,027 B1 | 8/2003 | Tsantrizos et al. |
| 6,608,067 B1 | 8/2003 | Tung et al. |
| 6,617,309 B2 | 9/2003 | Tung et al. |
| 6,653,127 B1 | 11/2003 | Malcolm et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena et al. |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,909,000 B2 | 6/2005 | Farmer et al. |
| 6,911,428 B2 | 6/2005 | Zhu et al. |
| 6,914,122 B2 | 7/2005 | Venkatraman et al. |
| 6,919,423 B2 | 7/2005 | Llinas-Brunet et al. |
| 6,939,692 B2 | 9/2005 | Bathe et al. |
| 6,939,854 B2 | 9/2005 | Priestley |
| 7,012,066 B2 | 3/2006 | Saksena et al. |
| 7,034,178 B2 | 4/2006 | Faber et al. |
| 7,091,184 B2 | 8/2006 | Llinas-Brunet et al. |
| 7,105,302 B2 | 9/2006 | Bathe et al. |
| 7,109,172 B2 | 9/2006 | Britt et al. |
| 7,119,073 B2 | 10/2006 | Colarusso et al. |
| 7,122,627 B2 | 10/2006 | Priestley |
| 7,169,760 B2 | 1/2007 | Saksena et al. |
| 7,208,600 B2 | 4/2007 | Cottrell et al. |
| 7,241,796 B2 | 7/2007 | Farmer et al. |
| 7,244,721 B2 | 7/2007 | Saksena et al. |
| 7,250,520 B2 | 7/2007 | Wallace |
| 7,273,885 B2 | 9/2007 | Pitlik et al. |
| 7,288,624 B2 | 10/2007 | Bemis et al. |
| 7,365,092 B2 | 4/2008 | Cottrell et al. |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung et al. |
| 7,504,378 B2 | 3/2009 | Llinas-Brunet et al. |
| 7,517,990 B2 * | 4/2009 | Ito et al. ............... 546/184 |
| 7,592,316 B2 | 9/2009 | Njoroge et al. |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley et al. |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0119752 A1 | 6/2003 | Farmer et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris et al. |
| 2004/0067901 A1 | 4/2004 | Bhat et al. |
| 2004/0072788 A1 | 4/2004 | Bhat et al. |
| 2004/0077600 A1 | 4/2004 | Tung et al. |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet |
| 2004/0266731 A1 | 12/2004 | Tung et al. |
| 2005/0020503 A1 | 1/2005 | Llinas-Brunet et al. |
| 2005/0049220 A1 | 3/2005 | Stuyver et al. |
| 2005/0059606 A1 | 3/2005 | Saksena et al. |
| 2005/0062522 A1 | 3/2005 | Haider et al. |
| 2005/0080005 A1 | 4/2005 | Llinas-Brunet et al. |
| 2005/0080017 A1 | 4/2005 | Cottrell et al. |
| 2005/0090450 A1 | 4/2005 | Farmer et al. |
| 2005/0107304 A1 | 5/2005 | Britt et al. |
| 2005/0112093 A1 | 5/2005 | Ette et al. |
| 2005/0119189 A1 | 6/2005 | Cottrell et al. |
| 2005/0119318 A1 | 6/2005 | Hudyma et al. |
| 2005/0120398 A1 | 6/2005 | Kalkeri et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine et al. |
| 2005/0197301 A1 | 9/2005 | Njoroge et al. |
| 2005/0215486 A1 | 9/2005 | Cottrell et al. |
| 2005/0222236 A1 | 10/2005 | Tsantrizos et al. |
| 2005/0249702 A1 | 11/2005 | Njoroge et al. |
| 2005/0287514 A1 | 12/2005 | Bryn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui et al. |
| 2006/0105978 A1 | 5/2006 | Chu et al. |
| 2006/0205672 A1 | 9/2006 | Saksena et al. |
| 2006/0211629 A1 | 9/2006 | Britt et al. |
| 2007/0082929 A1 * | 4/2007 | Gant et al. ............... 514/338 |
| 2007/0087093 A1 | 4/2007 | Tanoury |
| 2007/0105781 A1 | 5/2007 | Lyons et al. |
| 2007/0161789 A1 | 7/2007 | Cottrell et al. |
| 2007/0179167 A1 | 8/2007 | Cottrell et al. |
| 2007/0191381 A1 | 8/2007 | Tung et al. |
| 2007/0197695 A1 * | 8/2007 | Potyen et al. ............... 524/110 |
| 2007/0212683 A1 | 9/2007 | Connelly |
| 2007/0218012 A1 | 9/2007 | Bittorf et al. |

| | | | | | | |
|---|---|---|---|---|---|---|
| 2007/0218138 | A1 | 9/2007 | Bittorf et al. | WO | WO 2004/026896 | 4/2004 |
| 2007/0225297 | A1 | 9/2007 | Perni et al. | WO | WO 2004/030670 | 4/2004 |
| 2007/0231262 | A1 | 10/2007 | Lin et al. | WO | WO 2004/032827 | 4/2004 |
| 2007/0243166 | A1 | 10/2007 | Llinas-Brunet et al. | WO | WO 2004/037855 | 5/2004 |
| 2007/0244334 | A1 | 10/2007 | Tanoury et al. | WO | WO 2004/039833 | 5/2004 |
| 2007/0292933 | A1 | 12/2007 | Pitlik et al. | WO | WO 2004/072243 | 8/2004 |
| 2008/0045480 | A1 | 2/2008 | Farmer et al. | WO | WO 2004/089974 | 10/2004 |
| 2008/0070972 | A1 | 3/2008 | Kadiyala et al. | WO | WO 2004/092161 | 10/2004 |
| 2008/0125376 | A1 | 5/2008 | Cottrell et al. | WO | WO 2004/093798 | 11/2004 |
| 2008/0167480 | A1 | 7/2008 | Wallace | WO | WO 2004/094452 | 11/2004 |
| 2008/0267915 | A1 | 10/2008 | Lin et al. | WO | WO 2004/103996 | 12/2004 |
| 2008/0311079 | A1 | 12/2008 | Perni et al. | WO | WO 2004/113365 | 12/2004 |
| 2009/0022688 | A1 | 1/2009 | Farmer et al. | WO | WO 2005/007681 | 1/2005 |
| 2009/0143312 | A1 | 6/2009 | Tung et al. | WO | WO 2005/010029 | 2/2005 |
| 2009/0191555 | A1 | 7/2009 | Lin et al. | WO | WO 2005/021584 | 3/2005 |
| 2009/0247468 | A1 | 10/2009 | Bittorf et al. | WO | WO 2005/028501 | 3/2005 |
| | | | | WO | WO 2005/028502 | 3/2005 |
| FOREIGN PATENT DOCUMENTS | | | | WO | WO 2005/030796 | 4/2005 |
| | | | | WO | WO 2005/035525 | 4/2005 |
| EP | | 0417721 | 3/1991 | WO | WO 2005/037214 | 4/2005 |
| EP | | 0675112 | 10/1995 | WO | WO 2005/037860 | 4/2005 |
| GB | | 1367674 | 9/1974 | WO | WO 2005/042570 | 5/2005 |
| JP | | 09124691 | 5/1997 | WO | WO 2005/046712 | 5/2005 |
| WO | WO 92/12140 | | 7/1992 | WO | WO 2005/051410 | 6/2005 |
| WO | WO 93/25574 | | 12/1993 | WO | WO 2005/051980 | 6/2005 |
| WO | WO 94/14436 | | 7/1994 | WO | WO 2005/054430 | 6/2005 |
| WO | WO 95/07696 | | 3/1995 | WO | WO 2005/058821 | 6/2005 |
| WO | WO 95/09614 | | 4/1995 | WO | WO 2005/070955 | 8/2005 |
| WO | WO 96/11697 | | 4/1996 | WO | WO 2005/073195 | 8/2005 |
| WO | WO 97/17364 | | 5/1997 | WO | WO 2005/073216 | 8/2005 |
| WO | WO 97/40028 | | 10/1997 | WO | WO 2005/077969 | 8/2005 |
| WO | WO 97/43310 | | 11/1997 | WO | WO 2005/085242 | 9/2005 |
| WO | WO 98/13365 | | 4/1998 | WO | WO 2005/085275 | 9/2005 |
| WO | WO 98/17679 | | 4/1998 | WO | WO 2005/087721 | 9/2005 |
| WO | WO 98/22496 | | 5/1998 | WO | WO 2005/087725 | 9/2005 |
| WO | WO 98/40381 | | 9/1998 | WO | WO 2005/087731 | 9/2005 |
| WO | WO 98/46630 | | 10/1998 | WO | WO 2005/095403 | 10/2005 |
| WO | WO 99/07733 | | 2/1999 | WO | WO 2005 107745 | 11/2005 |
| WO | WO 99/07734 | | 2/1999 | WO | WO 2005/113581 | 12/2005 |
| WO | WO 99/38888 | | 8/1999 | WO | WO 2005/123076 | 12/2005 |
| WO | WO 99/50230 | | 10/1999 | WO | WO 2006/000085 | 1/2006 |
| WO | WO 99/64442 | | 12/1999 | WO | WO 2006/007448 | 1/2006 |
| WO | WO 00/09543 | | 2/2000 | WO | WO 2006/007700 | 1/2006 |
| WO | WO 00/09558 | | 2/2000 | WO | WO 2006/007708 | 1/2006 |
| WO | WO 00/09588 | | 2/2000 | WO | WO 2007/016589 | 2/2007 |
| WO | WO 00/23421 | | 4/2000 | WO | WO 2007/025307 | 3/2007 |
| WO | WO 00/31129 | | 6/2000 | WO | WO 2008/106058 | 9/2008 |
| WO | WO 00/56331 | | 9/2000 | | | |

OTHER PUBLICATIONS

Tonn, Biological Mass Spectrometry vol. 22 Issue 11, pp. 633-642 (1993).*
Haskins, Biomedical Spectrometry vol. 9 Issue 7, pp. 269-277 (1982.*
Wolen, Journal of Clinical Pharmacology 1986; 26: 419-424.*
Browne, Journal of Clinical Pharmacology1998; 38: 213-220.*
Baillie, Pharmacology Rev.1981; 33: 81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39: 817-825.*
Honma et al., Drug Metab Dispos 15 (4): 551 (1987).*
Akahoshi, F., "Chymase Inhibitors and their Therapeutic Potential", Drugs of the Future, 27(8) (2009), pp. 765-770.
Anonymous, VPI internet press release Sep. 7, 2004.
Anonymous, newsrx internet article, May 31, 2004.
Arasappan, A., "Hepatitis C Virus NS3-4A Serine Protease Inhibitors: SAR of P'2 Moiety with Improved Potency", Bioorg. & Med. Chem. Let, vol. 15, (2005), pp. 4180-4184.
Avolio, S., "Inhibitors of hepatitis C virus NS3/4A: a-Ketoamide based macrocyclic inhibitors," Bioorganic & Medicinal Chemistry Letters (2009), 19, pp. 2295-2298.
Baillie, T. A., "The Use of Stable Isotopes in Pharmacological Research," Pharmacological Reviews, 33(2) (1981), pp. 81-132.
Bastos, M., "Inhibitors of Human Heart Chymase Based on a Peptide Library", Proc. Natl. Acad. Sci. USA, vol. 92 (1995), pp. 6738-6742.

(Additional WO entries:)
WO WO 00/59929 10/2000
WO WO 01/02424 1/2001
WO WO 01/07407 2/2001
WO WO 01/32691 5/2001
WO WO 01/40262 6/2001
WO WO 01/40266 6/2001
WO WO 01/58929 8/2001
WO WO 01/64678 9/2001
WO WO 01/74768 10/2001
WO WO 01/77113 10/2001
WO WO 01/81325 11/2001
WO WO 02/07761 1/2002
WO WO 02/08187 1/2002
WO WO 02/08198 1/2002
WO WO 02/08244 1/2002
WO WO 02/08251 1/2002
WO WO 02/08256 1/2002
WO WO 02/18369 3/2002
WO WO 02/48116 6/2002
WO WO 02/48157 6/2002
WO WO 02/48172 6/2002
WO WO 02/060926 8/2002
WO WO 02/079234 10/2002
WO WO 03/003804 1/2003
WO WO 03/006490 1/2003
WO WO 03/020298 3/2003
WO WO 03/062228 7/2003
WO WO 03/062265 7/2003
WO WO 03/064416 8/2003
WO WO 03/064455 8/2003
WO WO 03/064456 8/2003
WO WO 03/087092 10/2003

Beak, P., "Complex Induced Proximity Effects: Enantioselective Syntheses Based on Asymmetric Deprotonations of N-Boc-Pyrrolidines", J. Amer. Chem. Soc., vol. 116 (1994), pp. 3231-3239.

Behrens, C., "Selective Transformations of 2,3-Epoxy Alcohols and Related Derivatives. Strategies for Nucleophilic Attack at Carbon-3 or Carbon-2", J. Org.Chem., vol. 50 (1985), pp. 5696-5704.

Bergmeier, S.C., "Synthesis of Bicyclic Proline Analogs Using a formal [3+2] Intramolecular Aziridine-Allylsilane Cycloaddition Reaction", Tetrahedron, vol. 55, No. 26 (1999), pp. 8025-8038.

Blair, W., "5th Antiviral Drug Discovery and Development Summit," Expert Opinion on Investigational Drugs 13(8) (2004), pp. 1065-1069.

Blankley, C.J., "Synthesis and Structure-Activity Relationships of Potent New Abgiotensin Converting Enzyme Inhibitors Containing Saturated Bicyclic Amino Acids", J. of Medicinal Chem., vol. 30 (1987).

Browne, T.R., "Stable Isotope Techniques in Early Drug Development: An Economic Evaluation," Journal of Clinical Pharmacology, 38 (1998) pp. 213-220.

Cacciola, J., "The Synthesis of Lysine a-Ketoamide Thrombin Inhibitors via an Epoxy Amide Ring Opening", Tetrahedron Let., vol. 38, No. 33 (1997), pp. 5741-5744.

Chawla, et al., "Challenges in Polymorphism of Pharmaceuticals", CRIPS vol. 5, No. 1, Jan.-Mar. 2004, 4 pages.

Chen, S., "Synthesis and Evaluation of Tripeptidyl a-Ketoamides as Human Rhinovirus 3C Protease Inhibitors", Bioorg. & Med. Chem. Letters, vol. 13, No. 20 (2003), pp. 3531-3536.

Chen, S., "Discovery of Small-Molecule Inhibitors of HCV NS3-4A Protease as Potential Therapeutic Agents against HCV Infection," Current Medicinal Chemistry (2005), 12(20), pp. 2317-2342.

Chen, S., "P1 and P1' Optimization of [3,4]-Bicycloproline P2 Incorporated Tetrapeptidyl a-ketoamide Based HCV Protease Inhibitors," Letters in Drug Design and Discovery (2005), 2(2), pp. 118-123.

Cheng, W., "Stereoselective Synthesis of Unnatural Spiroisoxazolinoproline-Based Acids and Derivatives", J. Org. Chem., (2002), pp. 5673-5677.

Cherrah, Y., "Study of Deuterium Isotope Effects on Protein Binding by Gas Chromatography/Mass Spectrometry. Caffeine and Deuterated Isotopomers," Biomedical and Environmental Mass Spectrometry, 14 (1987), pp. 653-657.

Collado, I., "Stereocontrolled Synthesis of 4-Substituted (±)-Kainic Acids", Journal of Organic Chem., vol. 63 (1998).

Davis, G. "Future Options for the Management of Hepatitis C", Seminars in Liver Disease, vol. 19, Supp. 1 (1999), pp. 103-112.

Dixon, S. M., "A Spiroisoazolinoproline-based Amino Acid Scaffold for Solid Phase and One-Bead-One-Compound Library Synthesis" Journal of Combinatorial Chemistry, 9 (2007) pp. 143-157.

Dunsdon, R., "Solid Phase Synthesis of Aminoboronic Acids: Potent Inhibitors of the Hepatitis C Virus NS3 Proteinase", Bioorganic & Medicinal Chemistry Letters, 10 (2000), pp. 1577-1579.

Dyck, L., "Effects of Deuterium Substitution on the Catabolism of β-Phenylethylamine: An in vivo study," Journal of Neurochemistry, 46(2) ((1986), pp. 399-404.

Elemes, Yiannis, et al. Synthesis of enantiopure alpha-deuteriated Boc-L-amino acids, J. Chem. Soc., Perkin Trans. 1., 537-540, 1995.

Esch, P.M., "Reductive Cyclization of Carbon-Centered Glycine Radicals; A Novel Synthetic route to Cyclic a-Amino Acids", Tetrahedron, vol. 48, No. 22 (1992), pp. 4659-4676.

Farmer, L., "Inhibitors of Hepatitis C Virus NS3-4A Protease: P2 Proline Variants," Letters in Drug Design and Discovery (2005), 2, pp. 497-502.

Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.

Gallagher, D., "Complex-Induced Proximity Effects: Evidence for a Prelithiation Complex and a Rate-Determining Deprotonation in the Asymmetric Lithiation of Boc-Pyrrolidine by an -PrLi/(−) Sparteine Complex", J. Org. Chem., vol. 60 (1995), pp. 7092-7093.

Gallagher, D., "Chiral Organolithium Complexes: The Effect of Ligand Structure on the Enantioselective Deprotonation of Boc-Pyrrolidine", J. Org. Chem., vol. 60 (1995), pp. 8148-8154.

Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(1H-Imidazol-1-yl)benzoyl]-7-isopropyl-3,7-diazabicyclo[3.3.1]nonane Dihydroperchlorate", J. Med. Chem, vol. 39, No. 13 (1996), pp. 2559-2570.

Golina, S., "Vulcanisation of Poly(diethyl-n-butylamino) Phosphazenes", Internat'l Polymer Science & Tech., vol. 18, No. 3 (1991), pp. T20-T22.

Gouyette, A., "Synthesis of Deuterium-labelled Elliptinium and its Use in Metabolic Studies," Biomedical and Environmental Mass Spectrometry, 15 (1988), pp. 243-247.

Han, W., "a-Ketoamides, a-Ketoesters and a-Diketones as HCV NS3 Protease Inhibitors", Bioorganic & Medicinal Chemistry Letters 10 (2000), pp. 711-713.

Haskins, N., "The Application of Stable Isotopes in Biomedical Research," Biomedical Mass Spectroscopy, 9(7) (1982), pp. 269-277.

Honma, S., "The Metabolism of Roxatidine Acetate Hydrochloride: Liberation of Deuterium from the Piperadine Ring during Hydroxylation," Drug Metabolism and Deposition, 15(4) (1987), pp. 551-559.

Janssen, H.L.A., "Suicide Associated with a-Interferon Therapy for Chronic Viral Hepatitis", J. Hepatol., 21 (1994), pp. 241-243.

Johansson, A., "Acyl Sulfonamides as Potent Protease Inhibitors of the Hepatitis C Virus Full-Length NS3 (Protease-Helicase/NTPase): A comparative Study of Different C-Terminals", Bioorganic & Medicinal Chemistry, 11 (2003), pp. 2551-2568.

Johansson, P., "Potent inhibitors of the hepatitis C virus NS3 protease: Use of a novel P2 cyclopentane-derived template," Bioorganic & Medicinal Chemistry (2006), 14, pp. 5136-5151.

Kakei, H., "Catalytic Asymmetric Epoxidation of a, β-Unsaturated Esters Using an Yttrium-Biphenyldiol Complex", J. Am. Chem. Soc., vol. 127 (2005), pp. 8962-8963.

Kalkeri, G., "Expression of HCV Protease in the Liver of Mice Results in Liver Injury Which can be Inhibited by VX-950, A Vertex HCV Protease Inhibitor," AALSD Abstracts, Hepatology (2004), 40(1), pp. 281A.

Kamandi, E., "Die Synthese von β-Phenyl-Isoserinen Durch Ammonolyse von β-Phenyl-Glycidestem, I.", Archiv de Pharmazie, vol. 307 No. 11 (1974), pp. 871-878.

Kao, J.H., "Efficacy of Consensus Interferon in the Treatment of Chronic Hepatitis", J. Gastroenterol. Hepatol, 15 (2000), pp. 1418-1423.

Kerrick, S., "Asymmetric Deprotonations: Enantioselective Syntheses of 2-Substituted (tert-Butoxycarbonyl) pyrrolidines", J. Amer. Chem. Soc., vol. 113 (1991), pp. 9703-9710.

Kieffer, T., "Genetic Heterogeneity in the HCV NS3 Protease of Untreated Genotype 1 Patients has Little Effect on the Sensitivity to VX-950", Hepatol, vol. 42 (2005), p. 537A.

Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.

Kieffer, T., "Combination of Telaprevir (VX-950) and Peg-lfn-Alfa Suppresses both Wild-Type Virus and Resistance Variants in HCV Genotype 1-Infected Patients in a 14-Day Phase 1B Study", Hepatol. 44, Supp.2 (2006), p. 222A.

Kieffer, Genetic Heterogeneity in the HCV Ns3 Protease of Untreated Genotype 1 Patients Has Little Effect on the Sensitivity of the VX-950, 12th Internat'l. Conf. on Hep. C Virus and Related Viruses, Montreal, Canada, Oct. 2-6, 2005.

Kim, J., "Hepatitis C Virus NS3 RNA Helicase Domain with a bound Oligonucleotide: The Crystal Structure Provides Insights into the Mode of Unwinding", Structure, vol. 6, No. 1, (1998), pp. 89-100.

Kim, J., "Crystal structure of the hepatitis C virus NS3 protease domain complexed with a synthetic NS4A cofactor peptide," Cell, vol. 87 (1996), pp. 343-355; [and Kim, J. "Erratum," Cell, vol. 89, No. 1 (1997), p. 159.

Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.

Kwong, A.D., "Structure and Function of Hepatitis C Virus NS3 Helicase", Top Microbiol. Immunol., vol. 242, (2000), pp. 171-196.

Kwong, A.D., "Hepatitis C Virus NS3/4A Protease", Antiviral Res., vol. 40 (1998), pp. 1-18.

Kwong, A.D., "Erratum: Hepatitis C Virus NS3/4A Protease", Antiviral Res., vol. 41 (1999), pp. 65-84.

Kwong, A.D., "An Orally Bioavailable Inhibitor of the HCV NS3-4a Protease; a Potential HCV Therapeutic", 5th Antivir. Drug Disc. and Devel. Summit, (Mar. 30, 2004).

Kwong, A.D., "HCV Protease Inhibitors: Activity and Resistance," 13th Conference on Retroviruses and Opp. Infections (CROI), Denver, CO, Feb. 5-8, 2006.

Kwong, A.D., "Beyond Interferon and Ribavirin: Antiviral Therapies for Hepatitis C Virus", Drug Disc. Today: Ther. Strategies, vol. 3 (2006), pp. 211-220.

Kwong, A.D., "VX-950: A Novel Hepatitis C Protease Inhibitor", HepDART (2005).

Lamar, J., "Novel P4 Truncated Tripeptidyl a-ketoamides as HCV Protease Inhibitors", Bio. & Med. Chem. Let, vol. 14 No. 1 (2004), pp. 263-266.

Landro, J.A. "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 36 (1997) pp. 9340-9348.

Laplante, S., "NMR Line-Broadening and Transferred NOESY as a Medicinal Chemistry Tool for Studying Inhibitors of the Hepatitis C Virus NS3 Protease Domain", Bioorganic & Medicinal Chemistry Letters, 10 (2000), pp. 2271-2274.

Lavanchy, D., "Global Surveillance and control of Hepatitis C", J. Viral Hepatitis, 6 (1999), pp. 35-47.

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Internat'l Symposium on Viral Hep. and Liver Dis., (2006).

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol., vol. 131, No. 3 (2006), pp. 950-951.

Lehmann, Über die chemischen und biologischen Eigenschaften einiger a-Aminoketone, Helvetica Chimica Acta., vol. 33 (1950), pp. 1217-1226.

Lin, C., "Structure-Based Mutagenesis Study of Hepatitis C Virus NS3 Helicase", J. Virol., vol. 73, No. 10 (1999), pp. 8798-8807.

Lin, K., "Combination of a Hepatitis C Virus NS3-NS4A Protease Inhibitor and Alph Interferon Synergistically Inhibits Viral RNA Replication and Facilitates Viral RNA Clearance in Replicon Cells", Antimicrob. Agents Chemo., vol. 48 (2004), pp. 4784-4792.

Lin, K., "VX-950, a Novel Hepatitis C Virus (HCV) NS3-4A Protease Inhibitor, Exhibits Potent Antiviral Activities in HCV Replicon Cells", Antimicrob. Agents Chemo, vol. 50, No. 5 (2006), pp. 1813-1822.

Lin, K., "VX-950: A Tight-Binding HCV Protease Inhibitor with a Superior Sustained Inhibitory Response in HCV Replicon Cells", Hepatol, vol. 38 (2003), p. 222A.

Lin, C., "Discovery and Development of VX-950, a Novel, Covalent and Reversible Inhibitor of Hepatitis C Virus NS3-4A Serine Protease", Infect. disord. Drug Targets, vol. 6, No. 1 (2006), pp. 3-16.

Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.

Llinàs-Brunet, M., "Highly Potent and Selective Peptide-Based Inhibitors of the Hepatitis C Virus Serino Protease: Towards Smaller Inhibitors", Bioorganic & Medicinal Chemistry Letters, 10 (2000), pp. 2267-2270.

Llinàs-Brunet, M., "Peptide-Based Inhibitors of the Hepatitis C Virus Serine Protease", Bioorganic & Medicinal Chemistry Letters, 8 (1998), pp. 1713-1718.

Llinàs-Brunet, M., "Studies on the C-Terminal of Hexapeptide Inhibitors of the Hepatitis C virus Serine Protease", Bioorganic & Medicinal Chemistry Letters, 8 (1998), pp. 2719-2724.

Lohmann, F. "Replication of Subgenomic Hepatitis C Virus RNAs in a Hepatoma Cell Line", Science, 285.5454 (1999) p. 110.

Marigo, M., "Asymmetric Organocatalytic Epoxidation of a,β-Unsaturated Aldehydes with Hydrogen Peroxide", J. Am. Chem. Soc., vol. 127, No. 19 (2005), pp. 6964-6965.

Markland, W., "Broad-Spectrum Antiviral Activity of the IMP Dehydrogenase Inhibitor VX-497: a Comparison with Ribavirin and Demonstration of Antiviral Additivity with Alpha Interferon", Antimicrob. Ag. Chem., vol. 44, No. 4 (2000), pp. 859-866.

McLaren, R., "Infrared observations of circumstellar ammonia in OH/IR supergiants," Astrophysical Journal (1980), 240(3, Pt. 2), pp. L159-L163.

Mehdi, The Inbibition of Human Neutrophil Elastase and Cathepsin G by Peptidyl 1,2-Dicarbonyl Derivatives, Biochem & Biophys. Res. Comm., vol. 166, No. 2 (1990), pp. 595-660.

Monn, J., "A Concise, Stereocontrolled Thiazolium Ylide Approach to Kainic Acid", J. Organic Chem., vol. 59, No. 10 (1994), pp. 2773-2778.

Moradpour, D., "Current and Evolving Therapies for Hepatitis C", Eur. J. Gastroenterol. Hepatol., vol. 11 (1999), pp. 1199-1202.

Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Viral., vol. 71, No. 5 (1997), pp. 3767-3775.

Newman, A., "Solid-state Analysis of the Active Pharmaceutical Ingredient in Drug Products", vol. 8, No. 19 (2003), pp. 898-905.

Patent Abstracts of Japan, vol. 1997, No. 9, Sep. 30, 1997.

Perni, R., "NS3-4A Protease as a Target for Interfering with Hepatitis C Virus Replication", Drug News Perspect., vol. 13, No. 2 (2000), pp. 69-77.

Perni, R.B., "Inhibitors of Hepatitis C Virus NS3-4A Protease 1. Non-Charged Tetrapeptide Variants", Bioorganic & Medicinal Chemistry Letters, 13 (2003), pp. 4059-4063.

Perni, R.B., "Inhibitors of Hepatitis C Virus NS3-4A Protease 2. Warhead SAR and Optimization", Bioorganic & Medicinal Chemistry Letters, 14 (2004), pp. 1441-1446.

Perni, R.B., "Inhibitors of Hepatitis C Virus NS3-4A Part 3: P2 Proline Variants", Bioorganic & Medicinal Chemistry Letters, 14 (2004), pp. 1939-1942.

Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.

Perni, R., "VX-950: The Discovery of an Inhibitor of the Hepatitis C NS3-4A Protease and a Potential Hepatitis C Virus Therapeutic", Hepatology, vol. 38 (2003) p. 624A.

Perni, R., "Toward Smaller HCV NS3-4A Protease Inhibitors: 3-Substituted Proline-based Tripeptide Scaffolds," Abstracts of Papers, 229th ACS National Meeting, San Diego, CA, United States, Mar. 13-17, 2005 (2005), MEDI-350.

Perni, R., "The Design of Inhibitors of the HCV NS3-4A Protease: The Identification of a Clinical Development Candidate, VX-950," ACS National Medicinal Chemistry Symposium, Madison, WI, Jun. 2004 (2004).

Perni, R., "Inhibitors of hepatitis C virus NS3-4A protease. Effect of P4 capping groups on inhibitory potency and pharmacokinetics," Bioorganic & Medicinal Chemistry Letters (2007), 17(12), pp. 3406-3411.

Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.

Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.

Pieniaszek, H., "Moricizine Bioavailability via Sumultaneous, Dual, Stable isotope Administration: Bioequivalence Implications," Journal of Clinical Pharmacology, 39 (1999), pp. 817-825.

Pippel, D., "Complex-Induced Proximity Effects: Steroselective Carbon-Carbon Bond Formation in Chiral Auxiliary Mediated β-Lithiation-Substitution Sequences of β-Substituted Secondary Carboxamides", J. Org. Chem., vol. 63 (1998), pp. 2-3.

Poliakov, A. "Structure-Activity Relationships for the Selectivity of Hepatitis C Virus NS3 Protease Inhibitors", Biochimica et Biophysica Acta, 1672 (2004), pp. 51-59.

Ramachandran, R., "Anti-Viral Activity of VX-950 Resolves Expression of an HCV-Associated Gene Signature", J. Hepatol, vol. 44, Supp. 2 (2006), p. S223.

Reesink, H., "Initial Results of a Phase 1B, Multiple-Dose Study of VX-950, a Hepatitis C Virus Protease Inhibitor", Gastroent, vol. 128, No. 4, Supp. 2 (2005), pp. A696-A697.

Reesink, H., "Rapid Decline of Viral RNA in Hepatitis C Patients Treated with VX-950: A Phase 1b, Placebo-Controlled Randomized Study", Gastroenterol., vol. 131, No. 4 (2006), pp. 997-1002.

Reesink, H., "Final Results of a Phase 1B, Multiple-Dose Study of VX-950, a Hepatitis C Virus Protease Inhibitor", Hepatology, vol. 42, No. 4, Supp. 1 (2005), pp. 234A-235A.

Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.

Renault, P.F., "Side Effects of Alpha Interferon", Seminars in Liver disease, 9 (1989), pp. 273-277.

Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.

Sagnard, I., "Enantioselective Synthesis of Cyclopropane a-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-3152.

Schneider, F. "Enhanced Plasma Concentration by Selective Deuteration of Rofecoxib in Rats," Arzneimittel-Forschung (Drug. Res.) vol. 56 (4) (2006), pp. 295-300.

Schneider, F. "Changed Phosphodiestarase Selectivity and Enhanced in vitro Efficacy by Selective Deuteraton of Sildenafil," Arzneimittel-Forschung (Drug. Res.) vol. 57 (6) (2007), pp. 293-298.

Taber, D., "Asymmetric Nucleophilic Epoxidation", Org. Chem. Highlights, (2004).

Takamizawa, A., "Structure and Organization of the Hepatitis C Virus Genome Isolated from Human Carriers", J. Virol., 65 (1991), pp. 1105-1113.

Taliani, M., "A continuous Assay of Hepatitis C Virus Protease Based on Resonance Energy Transfer Depsipeptide Substrates", Anal. Biochem., vol. 240 (1996), pp. 60-67.

Tan, S., "Strategies for Hepatitis C Therapeutic Intervention: Now and Next", Current Op. in Pharmacology, vol. 4, No. 5 (2004), pp. 465-470.

Tazulakhova, E.B., "Russian Experience in Screening, Analysis and Clinical Application of Novel Interferon Inducers", J. Interferon Cytokine Res., 21 (2001), pp. 65-73.

Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.

Tonn, G., "Simultaneous Analysis of Diphenhydramine and a Stable Isotope Analog (2H10)Diphenyhydramine Using Capillary Gas Chromatography with Mass Selective Detection in Biological Fluids from Chronically Instrumented Pregnant Ewes," Biological Mass Spectrometry, 22 (1993), pp. 633-642.

Toom, L., "Microwave-Assisted Raney Nickel Reduction of Bispidinone Thioketals to N,N'-Dialkylbispidines", Synthesis, vol. 12 (2006), pp. 2064-2068.

Udding, J.H., "Transition Metal-Catalyzed Chlorine Transfer Cyclizations of Carbon-Centered Glycine Radicals; A Novel Synthetic Route to Cyclic a-Amino Acids", Tetrahedron, vol. 50, No. 6 (1994), pp. 1907-1918.

Victor, F., "P1 and P3 optimization of novel bicycloproline P2 bearing tetrapeptidyl a-ketoamide based HCV protease inhibitors", Biorganic & Medicinal Chemistry Letters, 14 (2004), pp. 257-261.

Vishweshwar, P., "Pharmaceutical Co-Crystals", J. Pharm. Sci., vol. 95, No. 3 (2006), pp. 499-516.

Walker, M.A., "Hepatitis C Virus: An Overview of Current Approaches and Progress", DDT, 4 (1999), pp. 518-529.

Wang, Z., "Asymmetric Epoxidation of trans-β-Methylstyrene and 1-Phenylcyclohexene Using a D-Fructose-Derived Ketone: (R,R)-trans-β-Methylstyrene Oxide and (R,R)-1-Phenylcyclohexene Oxide", Org. Syntheses, vol. 80 (2003), pp. 9-13.

Weiland, O., "Interferon Therapy in Chronic Hepatitis C Virus Infection", FEMS Microiol. Rev., 14 (1994), pp. 279-288.

White, P.W. "Blunting the Swiss Army Knife of Hepatitis C Virus: Inhibitors of NS3/4A Protease" Progress in Medicinal Chemistry 44 (2006), pp. 65-107.

Wolen, R., "The Application of Stable Isotopes to Studies of Drug Bioavailability and Bioequivalence," Journal of Clinical Pharmacology, 25 (1985), pp. 419-424.

Yao, N., "Molecular views of viral polyprotein processing revealed by the crystal structure of the hepatitis C virus bifunctional protease-helicase," Structure (1999), 7, pp. 1353-1363.

Yasuda, M., "Synthesis of Conformationally Defined Glutamic Acid Analogues from Readily Available Diels-Alder Adducts", Chem. and Pharm. Bulletin (1995), pp. 1318-1324.

Yip, Y., "Discovery of a Novel Bicycloproline P2 Bearing Peptidyl a-Ketoamide LY514962 as HCV Protease Inhibitor", Bio. & Med. Chem. Let, vol. 14, No. 1 (2005), pp. 251-256.

Yip, Y., "P4 and P1' Optimization of Bicycloproline P2 Bearing Tetrapeptidyl a-Ketoamides as HCV Protease Inhibitors", Bio. & Med. Chem. Let., vol. 14, No. 9 (2004), pp. 5007-5011.

Yun, C. "Oxidation of the antihistaminic drug terfenadine in human liver microsomes: Role of Cytochrome P-450 3A(4) in N-dealkylation and C-hydroxylation", Drug metabolism and Disposition, 21(3) (1993) pp. 403-409.

ISR dated May 2, 2002 for PCT/US2001/26008.
ISR dated Jun. 12, 2006 for PCT/US2005/039240.
ISR dated Feb. 6, 2007 for PCT/US2006/029988.
ISR dated Feb. 15, 2007 for PCT/US2006/0033770.
ISR dated Jul. 23, 2007 from PCT/US2007/006320.
ISR dated Aug. 3, 2007 from PCT/US2007/004995.
ISR dated Nov. 15, 2007 from PCT/US2007/006493.
ISR dated Nov. 16, 2007 from PCT/US2007/64294.
ISR dated Dec. 27, 2007 from PCT/US2006/032481.
ISR dated Jul. 7, 2008 for PCT/US2008/002541.
ISR dated Jan. 23, 2009 from PCT/US2008/002395.

* cited by examiner

DEUTERATED HEPATITIS C PROTEASE INHIBITORS

CROSS-REFERENCE

This application is a continuation of U.S. Ser. No. 11/717,991, filed Mar. 14, 2007. The present application claims the benefit under 35 U.S.C. §119 of U.S. Provisional Application Ser. No. 60/782,788, filed Mar. 16, 2006, U.S. Provisional Application Ser. No. 60/782,976, filed Mar. 16, 2006, and U.S. Provisional Application No. 60/844,771, filed Sep. 15, 2006.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31, (Suppl. 1), pp. 17-24 (1999)]. Nearly four million individuals may be infected in the United States alone [M. J. Alter et al., "The Epidemiology of Viral Hepatitis in the United States," Gastroenterol. Clin. North Am., 23, pp. 437-455 (1994); M. J. Alter "Hepatitis C Virus Infection in the United States," J. Hepatology, 31, (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, help process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently HCV NS3 serine protease is also an attractive target for drug discovery.

There are not currently any satisfactory anti-HCV agents or treatments. Until recently, the only established therapy for HCV disease was interferon treatment. However, interferons have significant side effects [M. A. Wlaker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (~25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

It was recently discovered that deuterium incorporation in a compound will reduce the rate of epimerization via a deuterium isotope effect, thus enhancing the concentration of the active isomers in vivo relative to its non-deuterated analogs.

SUMMARY OF THE INVENTION

The present invention relates to deuterated compounds of formula (I)

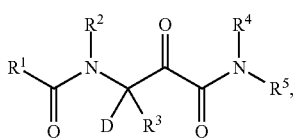

as well as pharmaceutically acceptable salts, prodrugs, and solvates thereof. In formula (I), D denotes a deuterium atom.

Referring to formula (I),

D denotes a deuterium atom;

$R^1$ is

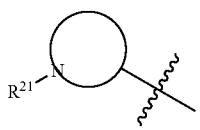

in which

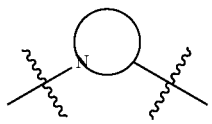

is an optionally substituted monocyclic azaheterocyclyl or optionally substituted multicyclic azaheterocyclyl, or optionally substituted multicyclic azaheterocyclenyl wherein the unsaturatation is in the ring distal to the ring bearing the $R^{21}$ moiety and to which the —C(O)—N($R^2$)—CDR$^3$—C(O)—C(O)—NR$^4$R$^5$ moiety is attached;

$R^{21}$ is $Q^3$-$W^3$-$Q^2$-$W^2$-$Q^1$; wherein

Each of $W^2$ and $W^3$ is independently a bond, —CO—, —CS—, —C(O)N($Q^4$)-, —CO$_2$—, —O—, —N($Q^4$)-C(O)—N($Q^4$)-, —N($Q^4$)-C(S)—N($Q^4$)-, —OC(O)NQ$^4$-, —S—, —SO—, —SO$_2$—, —N($Q^4$)-, —N($Q^4$)SO$_2$—, —N($Q^4$)SO$_2$N($Q^4$)-, and hydrogen when any of $W^2$ and $W^3$ is the terminal group;

Each of $Q^1$, $Q^2$, and $Q^3$ is independently a bond, an optionally substituted aliphatic, an optionally substituted heteroaliphatic, an optionally substituted cycloaliphatic, an optionally substituted aryl, an optionally substituted heteroaryl, an optionally substituted aralkyl, or an optionally substituted heteroaralkyl; or hydrogen when any of $Q^3$, $Q^2$, or $Q^1$ is the terminal group, provided that $Q^2$ is not a bond when both $W^3$ and $W^2$ are present; and Each of $R^2$, $R^3$, and $R^4$, independently, is H or a $C_{1-6}$ alkyl;

$R^5$ is H, alkyl, cycloalkyl, aryl optionally substituted with 1-4 alkyl groups, alkylaryl, aryl, amino optionally substituted with 1 or 2 alkyl groups; and $R^{21}$ is $Q^3$-$W^3$-$Q^2$-$W^2$-$Q^1$; wherein each of $W^2$ and $W^3$ is independently a bond, —CO—, —CS—, —C(O)N($Q^4$)-, —CO$_2$—, —O—, —N($Q^4$)-C(O)—N($Q^4$)-, —N($Q^4$)-C(S)—N($Q^4$)-, —OC(O)NQ$^4$-, —S—, —SO—, —SO$_2$—, —N($Q^4$)-, —N($Q^4$)SO$_2$—, —N($Q^4$)SO$_2$N($Q^4$)-, and hydrogen when any of $W^2$ and $W^3$ is the terminal group; each of $Q^1$, $Q^2$, and $Q^3$ is independently a bond, an optionally substituted aliphatic, an optionally substituted heteroaliphatic, an optionally substituted cycloaliphatic, an optionally substituted aryl, an optionally substituted heteroaryl, an optionally substituted aralkyl, or an optionally substituted heteroaralkyl; or hydrogen when any of $Q^3$, $Q^2$, or $Q^1$ is the terminal group, provided that $Q^2$ is not a bond when both $W^3$ and $W^2$ are present.

In some embodiments, $R^1$ is

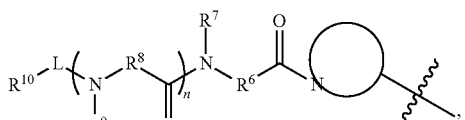

in which each of $R^6$ and $R^8$ is independently a bond; or optionally substituted (1,1- or 1,2-)cycloalkylene; or optionally substituted (1,1- or 1,2-)heterocyclylene; or methylene or ethylene, substituted with one substituent selected from the group consisting of an optionally substituted aliphatic group, an optionally substituted cyclic group and an optionally substituted aromatic group, and wherein the methylene or ethylene is further optionally substituted with an aliphatic group substituent;

each of $R^7$, $R^9$, and $R^{11}$ is independently hydrogen or optionally substituted aliphatic group;

$R^{10}$ is an optionally substituted aliphatic group, optionally substituted cyclic group or optionally substituted aromatic group;

L is —C(O)—, —OC(O)—, —NR$^{11}$C(O)—, —S(O)$_2$—, —NR$^{11}$S(O)$_2$—, or a bond; and n is 0 or 1.

In some embodiments, n is 1.

In some embodiments, $R^6$ is methylene substituted with one substituent selected from the group consisting of an optionally substituted aliphatic group, an optionally substituted cyclic group, and an optionally substituted aromatic group.

In some embodiments, $R^6$ is methylene substituted with isobutyl.

In some embodiments, $R^7$ is hydrogen.

In some embodiments, $R^8$ is methylene substituted with one substituent selected from the group consisting of an optionally substituted aliphatic group, an optionally substituted cyclic group, and an optionally substituted aromatic group. In some other embodiments, $R^8$ is methylene substituted with an optionally substituted cyclic group. In still some other embodiments, $R^8$ is methylene substituted with cyclohexyl.

In some embodiments, $R^9$ is hydrogen.

In some embodiments, L is —CO—.

In some embodiments, $R^{10}$ is an optionally substituted aromatic group.

In some embodiments, $R^{10}$ is selected from the group consisting of

In some embodiments, $R^{10}$ is optionally substituted pyrazinyl (e.g., 2-pyrazinyl).

In some embodiments, is a substituted monocyclic azaheterocyclyl.

In some other embodiments, is pyrrolidinyl substituted at the 3-position carbon atom with heteroaryloxy, wherein the heteroaryl is further optionally substituted with 1-4 halo groups.

In some embodiments, is

In some embodiments, is an optionally substituted multicyclic azaheterocyclyl.

In another embodiment,

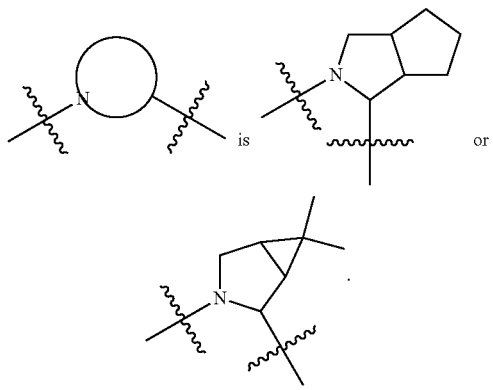

In some embodiments,

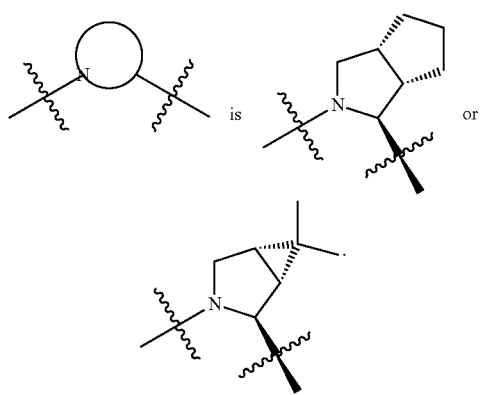

In another embodiment, R² is hydrogen, each of R⁴ and R⁵ independently is hydrogen or cyclopropyl. In another embodiment, R³ is propyl. In another embodiment, n is 0. In another embodiment, L is —NR¹¹C(O)— and R¹¹ is hydrogen. In another embodiment, R¹⁰ is an optionally substituted aliphatic group. In another embodiment, R¹⁰ is t-butyl. In another embodiment, the compound is

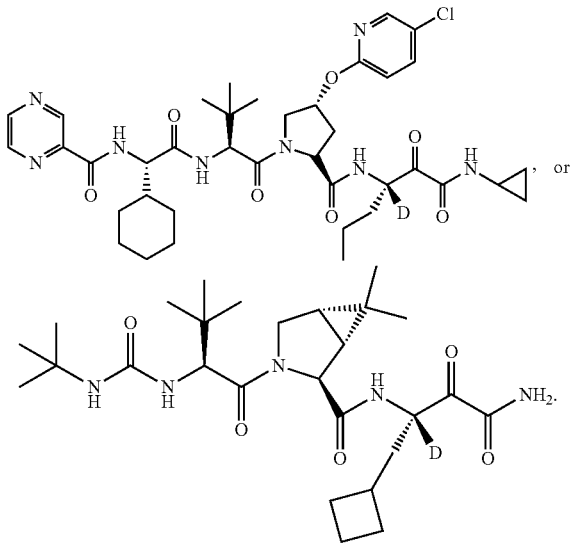

In some embodiments, R¹ is

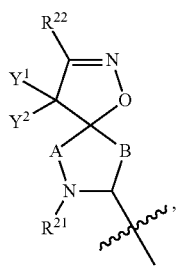

in which
A is —(CHX¹)$_a$—;
B is —(CHX²)$_b$—;
a is 0 to 3;
b is 0 to 3, provided that a+b is 2 or 3;
each of X¹ and X² is independently selected from hydrogen, optionally substituted C$_{1-4}$ aliphatic, and optionally substituted aryl;
each of Y¹ and Y² is independently hydrogen, optionally substituted aliphatic, optionally substituted aryl, amino, or —OQ⁴; wherein each Q⁴ is independently hydrogen or an optionally substituted aliphatic;
R²² is an optionally substituted aliphatic, an optionally substituted heteroaliphatic, an optionally substituted cycloaliphatic, an optionally substituted heterocycloaliphatic, an optionally substituted aryl, or an optionally substituted heteroaryl. In some embodiments, R²¹ is optionally substituted alkylcarbonyl.

The moiety

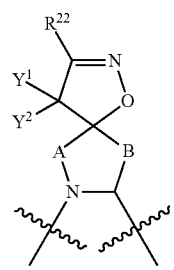

includes all of its stereospecific enantiomers, e.g.,

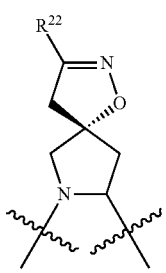

(when A and B are both CH₂, and Y¹ and Y² are both H).

In some embodiments, R²¹ is aminoalkylcarbonyl, haloalkylcarbonyl, arylalkylcarbonyl, arylalkylcarbonyl, cycloaliphaticalkylcarbonyl, or heterocycloaliphaticalkylcarbonyl, each of which is optionally substituted with 1-3 substituents. In some embodiments, $R^{21}$ is heterocycloalkyl-oxycarbonylamino-alkylcarbonyl, heteroaryl-carbonylamino-alkyl-carbonylamino-alkyl-carbonyl, bicycloaryl-sulfonylamino-alkylcarbonyl, aryl-alkoxy-carbonylamino-alkyl-carbonyl, alkyl-carbonylamino-alkyl-carbonyl, aliphatic-oxycarbonylamino-alkyl-carbonyl, cycloaliphatic-alkyl-aminocarbonylamino-alkyl-carbonyl, heteroaryl-carbonylamino-alkyl-carbonylamino-alkyl-carbonyl, alkyl-aminocarbonylamino-alkyl-carbonyl, or bicycloaryl-aminocarbonylamino-alkyl-carbonyl, each of which is optionally substituted with 1-3 substituents. In some embodiments, $R^{22}$ is an optionally substituted aliphatic, optionally substituted heteroaliphatic, optionally substituted cycloaliphatic, optionally substituted heterocycloaliphatic, optionally substituted aryl, or optionally substituted heteroaryl. In some embodiments, $R^{22}$ is optionally substituted phenyl, optionally substituted naphthyl, optionally substituted anthracenyl, optionally substituted naphthalene, or optionally substituted anthracene. In some embodiments, each of $X^1$, $X^2$, $Y^1$ and $Y^2$ is hydrogen, each of a and b is 1.

In some embodiments, $R^{21}$ is an optionally substituted alkylcarbonyl.

In some embodiments, $R^{21}$ is an aminoalkylcarbonyl, haloalkylcarbonyl, arylalkylcarbonyl, arylalkylcarbonyl, cycloaliphaticalkylcarbonyl, or heterocycloaliphaticalkylcarbonyl, each of which is optionally substituted with 1-3 substituents.

In some embodiments, $R^{21}$ is heterocycloalkyl-oxycarbonylamino-alkylcarbonyl, heteroaryl-carbonylamino-alkyl-carbonylamino-alkyl-carbonyl, bicycloaryl-sulfonylamino-alkylcarbonyl, aryl-alkoxy-carbonylamino-alkyl-carbonyl, alkyl-carbonylamino-alkyl-carbonyl, aliphatic-oxycarbonylamino-alkyl-carbonyl, cycloaliphatic-alkyl-aminocarbonylamino-alkyl-carbonyl, cycloaliphatic-alkyl-carbonylamino-alkyl-carbonyl, heteroaryl-carbonylamino-alkyl-carbonylamino-alkyl-carbonyl, alkyl-aminocarbonylamino-alkyl-carbonyl, or bicycloaryl-aminocarbonylamino-alkyl-carbonyl, each of which is optionally substituted with 1-3 substituents.

In some embodiments, $R^{22}$ is an optionally substituted aliphatic, optionally substituted heteroaliphatic, optionally substituted cycloaliphatic, optionally substituted heterocycloaliphatic, optionally substituted aryl, or optionally substituted heteroaryl.

In some embodiments, $R^{22}$ is optionally substituted phenyl, optionally substituted naphthyl, optionally substituted anthracenyl, optionally substituted naphthalene, or optionally substituted anthracene.

In some embodiments, each of $X^1$, $X^2$, $Y^1$, and $Y^2$ is hydrogen, each of a and b is 1.

In some embodiments, $R^{22}$ is an optionally substituted aliphatic, optionally substituted heteroaliphatic, optionally substituted cycloaliphatic, optionally substituted heterocycloaliphatic, optionally substituted aryl, or optionally substituted heteroaryl.

In an embodiment, the compound is

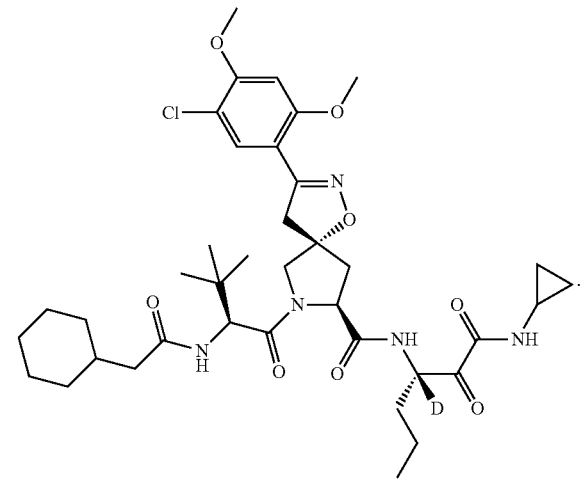

The deuterated compounds of this invention undergo slower epimerization than its non-deuterated counterparts. As shown below, the deuterated compound 1 very slowly converts to a non-deuterated intermediate which then converts to epimers 2 and 3. The epimers 2 and 3 then maintain in an equilibrium, which further slows the epimerization of the deuterated compound 1.

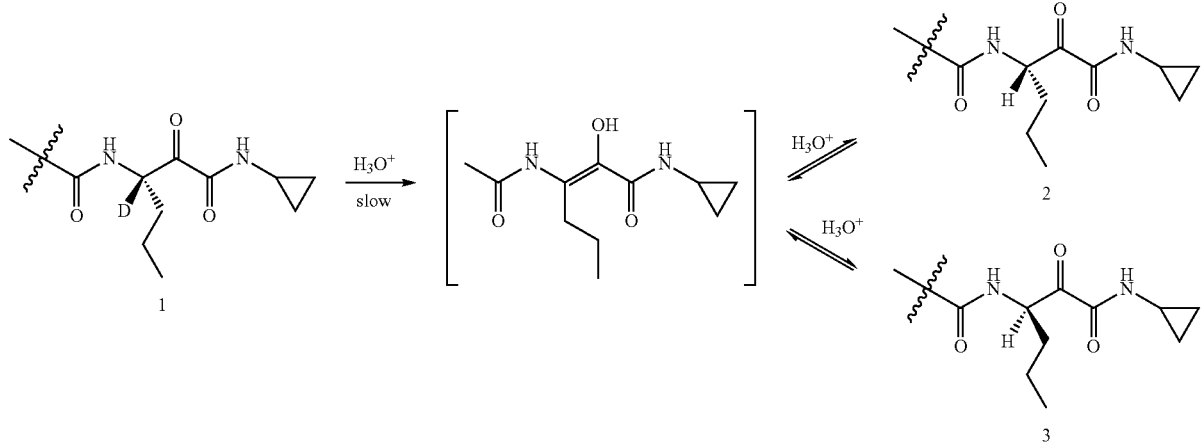

As a result of their slow epimerization, the deuterated compounds of this invention can enhance the concentration of the active isomers in vivo relative to its non-deuterated analogs.

In some embodiments, the deuterium enrichment is at least 50% in the compounds of this invention. In some embodiments, the deuterium enrichment is at least 80% in the compounds of this invention. In some embodiments, the deuterium enrichment is at least 90% in the compounds of this invention. In some embodiments, the deuterium enrichment is at least 99% in the compounds of this invention.

The invention also relates to a pharmaceutical composition comprising a pharmaceutically acceptable carrier and a compound of formula (I) or any of its embodiments described above.

The invention also relates to a method for increasing the concentration of the active isomer of a pharmaceutical agent in vivo, comprising administering to a patient in need thereof a deuterated isomer of the pharmaceutical agent in an amount sufficient to confer the pharmaceutical effect.

The invention also relates to a method for enhancing the bioavailability of a compound, comprising replacing a hydrogen atom that is bonded to a steric carbon atom in the compound with a deuterium atom. In one embodiment, the deuterated compound is of formula (I) or any of its embodiments described above.

The invention also relates to a method for inhibiting HCV protease, comprising contacting HCV protease with a deuterated compound of formula (I) or any of its embodiments described above.

The invention also relates to a method for treating a patient suffering from HCV infection or a condition mediated by HCV protease, comprising administering to the patient a pharmaceutically effective amount of a deuterated compound of formula (I) or any of its embodiments described above.

Also within the scope of this invention is a process for preparing an optically enriched compound of Formula 1, in which

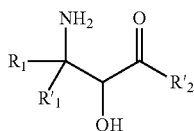

the carbon atoms alpha and beta to the carboxy group are stereocenters;
$R_1$ is independently H, optionally substituted aliphatic, optionally substituted cycloaliphatic, optionally substituted arylaliphatic, optionally substituted heteroaliphatic or optionally substituted heteroarylaliphatic;
$R'_1$ is deuterium,
$R'_2$ is —$NHR_2$ or —OE;
$R_2$ is H, an optionally substituted aliphatic, optionally substituted cycloaliphatic, optionally substituted arylaliphatic, optionally substituted heteroaliphatic or optionally substituted heteroarylaliphatic; and
E is a $C_{1-6}$ alkyl or benzyl;
The method includes the steps of:
a) forming a salt of a compound of Formula 1, and
b) crystallizing said salt to give a compound of greater than 55% enantiomeric excess.

In some embodiments, $R_1$ is $C_{1-6}$ alkyl, and $R'_2$ is —$NHR_2$ wherein $R_2$ is a $C_{1-6}$ alkyl or $C_{1-6}$ cycloalkyl. In some embodiments, $R_1$ is propyl and $R_2$ is cyclopropyl.

In some embodiments, the method further includes aminating a compound of Formula ii

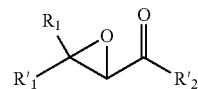

with an aminating reagent to provide a compound of Formula iii

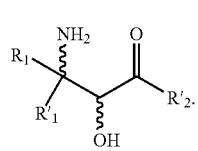

In still some embodiments, the aminating reagent is an azide salt and the intermediate azido compound is reduced by hydrogenation.

In some embodiments, the method further includes oxidizing an unsaturated compound

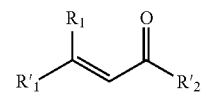

of Formula i
wherein $R'_2$ is —$NHR_2$ or —OE, wherein E is $C_{1-5}$ alkyl or optionally substituted benzyl, with an oxidizing reagent to provide a compound of Formula ii.

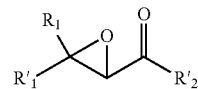

In some further embodiments, the oxidizing reagent comprises t-butyl hydroperoxide. In some further embodiments, the oxidizing reagent further includes a chiral reagent. In some further embodiments, the oxidizing reagent is a mixture of samarium (III) isopropoxide, triphenyl arsine oxide, S-(−) 1,1'-bi-2-naphthol and 4 Å molecular sieves. In some further embodiments, the oxidizing reagent comprises urea-hydrogen peroxide in the presence of trifluoroacetic anhydride.

In some further embodiments, the method further includes hydrolyzing the compound of Formula ii to give an acid and then converting the acid to an amide compound of Formula ii wherein $R'_2$ is —$NHR_2$.

Still within the scope of this invention is a process for preparing a compound of Formula 1

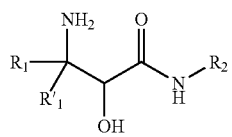

wherein:
R₁ is H, optionally substituted aliphatic, optionally substituted cycloaliphatic, optionally substituted arylaliphatic, optionally substituted heteroaliphatic or optionally substituted heteroarylaliphatic;

R'₁ is deuterium,

R₂ is H, optionally substituted aliphatic, optionally substituted cycloaliphatic, optionally substituted arylaliphatic, optionally substituted heteroaliphatic or optionally substituted heteroarylaliphatic; and the compound of Formula 1 has an enantiomeric excess of greater than 55%. The method includes the steps of:

a) oxidation of an unsaturated compound of Formula i

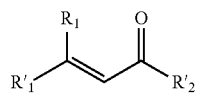

to provide a compound of formula ii

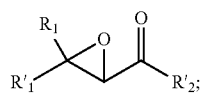

b) reacting a compound of Formula ii with an aminating reagent to provide a compound of Formula iii

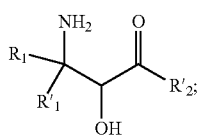

c) forming a salt of a compound of Formula iii with an optically active organic acid; and d) crystallizing said salt to give a compound of greater than 55% enantiomeric excess.

In some embodiments, the compound of Formula 1 is (2S, 3S)-3-amino-3-deutero-N-cyclopropyl-2-hydroxyhexanamide. In some embodiments, the organic acid is L-tartaric acid or deoxycholic acid.

Also within the scope of this invention is a process for preparing an optically enriched compound of Formula 1:

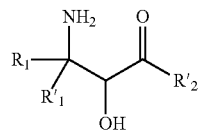

wherein:
the carbon atoms alpha and beta to the carboxy group are stereocenters;

R₁ is independently H, optionally substituted aliphatic, optionally substituted cycloaliphatic, optionally substituted arylaliphatic, optionally substituted heteroaliphatic or optionally substituted heteroarylaliphatic;

R'₁ is deuterium such that the deuterium enrichment is at least 50%;

R'₂ is —NHR₂ or —OE;

R₂ is H, optionally substituted aliphatic, optionally substituted cycloaliphatic, optionally substituted arylaliphatic, optionally substituted heteroaliphatic or optionally substituted heteroarylaliphatic; and E is $C_{1-6}$ alkyl or benzyl.

The method includes the steps of: a) forming a salt of a compound of Formula 1, and b) crystallizing said salt to give a compound of greater than 55% enantiomeric excess.

In some embodiments, R₁ is $C_{1-6}$ alkyl, and R'₂ is —NHR₂ wherein R₂ is a $C_{1-6}$ alkyl or $C_{1-6}$ cycloalkyl. In some embodiments, R₁ is propyl and R₂ is cyclopropyl.

In some embodiments, the method further includes the step of aminating a compound of Formula ii

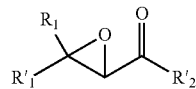

with an aminating reagent to provide a compound of Formula iii

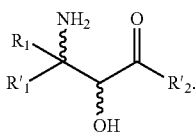

In some embodiments, the aminating reagent is an azide salt and the intermediate azido compound is reduced by hydrogenation.

In some embodiments, the method further includes the step of oxidizing an unsaturated compound of Formula i

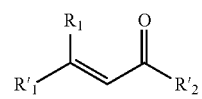

wherein R'₂ is —NHR₂ or —OE, wherein E is $C_{1-5}$ alkyl or optionally substituted benzyl, with an oxidizing reagent to provide a compound of Formula ii.

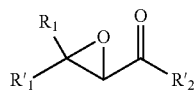

In some embodiments, the oxidizing reagent comprises t-butyl hydroperoxide. In some further embodiments, the oxidizing reagent further a chiral reagent. In some embodiments, the oxidizing reagent is a mixture of samarium (III) isopropoxide, triphenyl arsine oxide, S-(–) 1,1'-bi-2-naphthol and 4 Å molecular sieves. In some embodiments, the oxidizing reagent comprises urea-hydrogen peroxide in the presence of trifluoroacetic anhydride.

In some embodiments, R'2 is —OE. In some embodiments, R'$_2$ is —NHR$_2$.

In some embodiments, the method further includes hydrolyzing the compound of Formula ii to give an acid and then converting the acid to an amide compound of Formula ii wherein R'$_2$ is —NHR$_2$).

In some embodiments, the method further includes oxidizing a compound of Formula iv

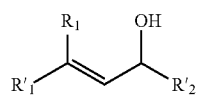

to give the compound of Formula ii. In some instance, the oxidation is conducted by using manganese dioxide.

In some embodiments, the method further includes reducing a compound of Formula v

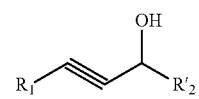

to give the compound of Formula iv. In some instance, the compound is reduced with Red-Al® and then quenched with deuterium oxide. As known in the art, "Red-Al®" refers to the compound [(CH$_3$OCH$_2$OCH$_2$)$_2$AlH$_2$]Na, which is commercial available, generally as a solution in toluene (e.g., 70% W/W). For more information about Red-Al®, see, e.g., Bates R. W. et al., *Tetrahedron,* 1990, 46, 4063.

Still within the scope of this invention is a process for preparing a compound of Formula 1

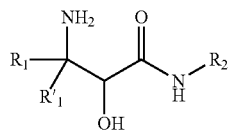

wherein:
R$_1$ is H, optionally substituted aliphatic, optionally substituted cycloaliphatic, optionally substituted arylaliphatic, optionally substituted heteroaliphatic or optionally substituted heteroarylaliphatic;
R'$_1$ is deuterium, R$_2$ is H, optionally substituted aliphatic, optionally substituted cycloaliphatic, optionally substituted arylaliphatic, optionally substituted heteroaliphatic or optionally substituted heteroarylaliphatic; and
the compound of Formula 1 has an enantiomeric excess of greater than 55%.

The method includes the steps of:
a) oxidation of an unsaturated compound of Formula i

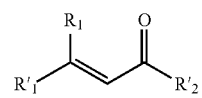

to provide a compound of formula ii

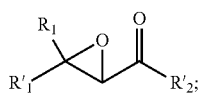

b) reacting a compound of Formula ii with an aminating reagent to provide a compound of Formula iii

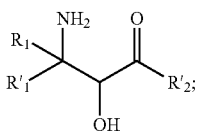

c) forming a salt of a compound of Formula iii with an optically active organic acid; and
d) crystallizing said salt to give a compound of greater than 55% enantiomeric excess.

In some embodiments, the compound of Formula 1 is (2S, 3S)-3-amino-3-deutero-N-cyclopropyl-2-hydroxyhexanamide. In some embodiments, the organic acid is L-tartaric acid or deoxycholic acid.

DETAILED DESCRIPTION OF THE INVENTION

I. Definitions

A. Terms

As used herein, the term "aliphatic" encompases alkyl, alkenyl and alkynyl.

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "amino" group refers to —$NR^XR^Y$ wherein each of $R^X$ and $R^Y$ is independently hydrogen, alkyl, cycloalkyl, (cycloalkyl)alkyl, aryl, aralkyl, heterocycloalkyl, (heterocycloalkyl)alkyl, heteroaryl, or heteroaralkyl. When the term "amino" is not the terminal group (e.g., alkylcarbonylamino), it is represented by —$NR^X$—. $R^X$ has the same meaning as defined above.

As used herein, an "aryl" group refers to phenyl, naphthyl, or a benzofused group having 2 to 3 rings. For example, a benzofused group includes phenyl fused with one or two $C_{4-8}$ cycloaliphatic moieties, e.g., 1, 2, 3, 4-tetrahydronaphthyl, indanyl, dihydroindanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl.

As used herein, cycloaliphatic encompasses cycloalkyl, cycloalkenyl and cycloalkynyl.

As used herein, a "cycloalkyl" group refers to an aliphatic carbocyclic ring of 3-10 (e.g., 4-8) carbon atoms. Examples of cycloalkyl groups include cyclopropyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.2.3]nonyl, A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]octenyl, and bicyclo[3.3.1]nonenyl. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, heterocycloaliphatic means heterocycloalkyl, heterocycloalkenyl and heterocycloalkynyl. As used herein, a "heterocycloalkyl" group refers to a 3- to 10-membered (e.g., 4- to 8-membered) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.03,7] nonyl. A "heterocycloalkenyl" group, as used herein, refers to a 3- to 10-membered (e.g., 4- to 8-membered) non-aromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl. In some instances, a substituent on the heterocycloalkyl or heterocycloalkenyl itself can be cyclic (which optionally contains one or more hetero atoms) such that the resultant substituted heterocycloalkyl or heterocycloalkenyl is a spiro ring system, e.g.,

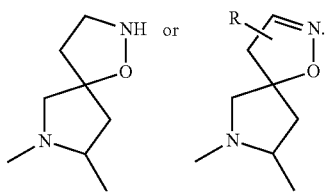

A "heteroaryl" group, as used herein, refers to a monocyclic, bicyclic, or tricyclic ring structure having 5 to 15 ring atoms wherein one or more of the ring atoms is a heteroatom, e.g., N, O, or S and wherein one or more rings of the bicyclic or tricyclic ring structure is aromatic. Some examples of heteroaryl are pyridyl, furyl, pyrrolyl, thienyl, thiazolyl, oxazolyl, imidazolyl, indolyl, 2,3-dihydroindolyl, quinolyl, 1,2-dihydroquinolyl, 1,2,3,4-tetrahydroquinolyl, tetrazolyl, benzofuryl, 2,3-dihydrobenzofuranyl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a foimyl group or alkyl-C(=O)— where "alkyl" has been defined previously. Acetyl and pivaloyl are examples of acyl groups.

As used herein, a "carbamoyl" group refers to a group having the structure —O—CO—$NR^xR^y$ or —$NR^x$—CO—O—$R^z$ wherein $R^x$ and $R^y$ have been defined above and $R^z$ can be alkyl, aryl, aralkyl, heterocycloalkyl, heteroaryl, or heteroaralkyl.

As used herein, a "carboxy" and a "sulfo" group refer to —COOH and —$SO_3H$, respectively.

As used herein, an "alkoxy" group refers to an alkyl-O— group where "alkyl" has been defined previously.

As used herein, a "sulfoxy" group refers to —O—SO—$R^X$ or —SO—O—$R^X$, where $R^X$ has been defined above.

As used herein, a sulfanyl group refers to —S—$R^X$, where $R^X$ has been defined above.

As used herein, a sulfinyl group refers to —S(O)—$R^X$, where $R^X$ has been defined above.

As used herein, a sulfonyl group refers to —$S(O)_2$—$R^X$, where $R^X$ has been defined above.

As used herein, a "halogen" or "halo" group refers to fluorine, chlorine, bromine or iodine.

As used herein, a "sulfamoyl" group refers to the structure —$S(O)_2$—$NR^xR^y$ or —$NR^x$—$S(O)_2$—$R^z$ wherein $R^x$, $R^y$, and $R^z$ have been defined above.

As used herein, a "sulfamide" group refers to the structure —$NR^X$—$S(O)_2$—$NR^YR^Z$ wherein $R^X$, $R^Y$, and $R^Z$ have been defined above.

As used herein, a "urea" group refers to the structure —$NR^X$—CO—$NR^YR^Z$ and a "thiourea" group refers to the structure —$NR^X$—CS—$NR^YR^Z$. $R^X$, $R^Y$, and $R^Z$ have been defined above.

As used herein, a "guanidino" group refers to the structure —N=C($NR^XR^y$)N($R^XR^y$) wherein $R^X$ and $R^Z$ have been defined above.

As used herein, the term "amidino group" refers to the structure —C=($NR^x$)N($R^xR^y$) wherein $R^X$ and $R^Y$ have been defined above.

As used herein, the term "oximino group" refers to the structure —C=N—ORx wherein $R^x$ has been defined above.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970).

As used herein, "patient" refers to a mammal, including a human.

An antagonist, as used herein, is a molecule that binds to the receptor without activating the receptor. It competes with the endogenous ligand(s) or substrate(s) for binding site(s) on the receptor and, thus inhibits the ability of the receptor to transduce an intracellular signal in response to endogenous ligand binding.

The phrase "optionally substituted" is used interchangeably with the phrase "substituted or unsubstituted." As described herein, compounds of the invention may optionally be substituted with one or more substituents, such as are illustrated generally above, or as exemplified by particular classes, subclasses, and species of the invention. Unless otherwise noted, each of the specific groups for the variables $R^1$, $R^2$, $R^3$, $R^4$, and $R^5$ in formula (I) may be optionally substituted with one or more substituents described herein. Each substituent of a specific group is further optionally substituted with one to three of halo, cyano, alkoxy, hydroxyl, nitro, haloalkyl, and alkyl. For instance, an alkyl group may be substituted with alkylsulfanyl and the alkylsulfanyl may be optionally substituted with one to three of halo, oxo, cyano, alkoxy, hydroxyl, nitro, haloalkyl, and alkyl. As an additional example, an alkyl may be substituted with a (cycloalkyl) carbonylamino and the cycloalkyl portion of a (cycloalkyl) carbonylamino may be optionally substituted with one to three of halo, cyano, oxo, alkoxy, hydroxyl, nitro, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

An N-oxide derivative or a pharmaceutically acceptable salt of each of the compounds of formula (I) is also within the scope of this invention. For example, a nitrogen ring atom of the imidazole or pyrazole core ring or a nitrogen-containing heterocyclyl substituent can form an oxide in the presence of a suitable oxidizing agent such as m-chloroperbenzoic acid or $H_2O_2$.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such acids include hydrochloric acid, hydrobromic acid, hydroiodic acid, sulfuric acid, methanesulfonic acid, phosphoric acid, p-bromophenyl-sulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to those skilled in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Compounds of formula (I) can also be, for example, in a form of achiral compounds, racemic mixtures, optically active compounds, pure diastereomers, or a mixture of diastereomers.

B. Abbreviations

The following abbreviations have the following meanings. If an abbreviation is not defined, it has its generally accepted meaning.

BEMP=2-tert-butylimino-2-diethylamino-1,3-dimethylperhydro-1,3,2-diazaphosphorine
Boc=t-butoxycarbonyl
BOP=benzotriazol-1-yloxy-tris(dimethylamino)phosphonium hexafluorophosphate
bd=broad doublet
bs=broad singlet
CDI=carbonyl diimidazole
d=doublet
dd=doublet of doublets
DIC=diisopropylcarbodiimide
DMF=dimethylformamide
DMAP=dimethylaminopyridine
DMSO=dimethylsulfoxide
EDCI=ethyl-1-(3-dimethyaminopropyl)carbodiimide
eq.=equivalents
EtOAc=ethyl acetate
g=grams
HOBT=1-hydroxybenzotriazole
DIPEA=Hunig's base=diisopropylethylamine
L=liter
m=multiplet
M=molar
max=maximum
meq=milliequivalent
mg=milligram
mL=milliliter
mm=millimeter
mmol=millimole
MOC=methoxyoxycarbonyl
N=normal
N/A=not available
ng=nanogram
nm=nanometers
OD=optical density
PEPC=1-(3-(1-pyrrolidinyl)propyl)-3-ethylcarbodiimide
PP-HOBT=piperidine-piperidine-1-hydroxybenzotrizole
psi=pounds per square inch
Ph=phenyl
q=quartet
quint.=quintet
rpm=rotations per minute
s=singlet
t=triplet
TFA=trifluoroacetic acid
THF=tetrahydrofuran
tlc=thin layer chromatography
μL=microliter
UV=ultra-violet II. Compounds of this Invention Generally, the deuterated compounds of this invention can be synthesized by methods known in the art as for synthesizing their non-deuterated forms, except that a deuterated starting material or a reacting reagent is used during the synthesis process. Examples of applicable methods include those described in U.S. Application No. 60/711,530; WO 02/18369; WO 07/022,459; Advanced Organic Chemistry, $2^{nd}$ Ed., p. 204, J. March, McGraw Hill, New York, N.Y., 1997; and Synthesis of A: Elemes and Ragnarsosson, J. of Chem. Soc., Perkin 1, 1996, 537.

All publications cited herein are incorporated by reference in their entireties.

Compounds of Formula I are prepared using known methods, for example, such as illustrated below in Scheme I.

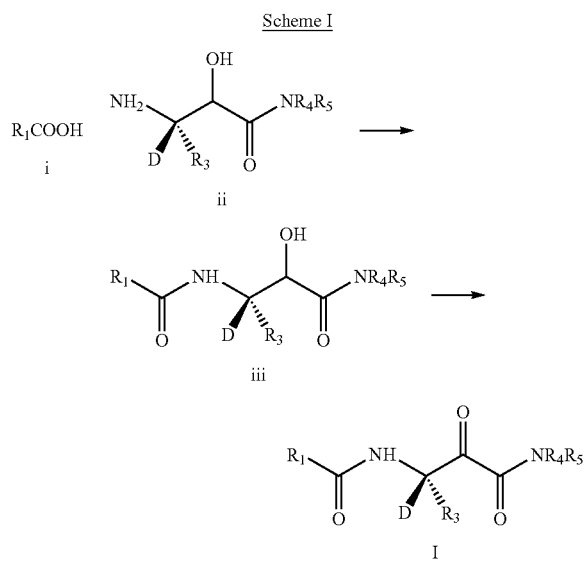

Scheme I

Referring to Scheme I, the acid of Formula i is reacted with a deuterated amino-alcohol-amide of Formula ii in the presence of a condensing reagent such as, for example, EDCI and HOSu to provide the hydroxy-amide of Formula iii. In some embodiments, the percent deuterium (D) enrichment as shown in ii is greater than 10%. In other embodiments the enrichment is from 10% to 99.95%, 40% to 99.95%, 50% to 99.95%, 60% to 99.95%, 80% to 99.95%, 90% to 99.95%, 93% to 99.95%, 97% to 99.95%, or 99-99.95%, or 99.95% or higher. Oxidation of iii with a suitable oxidizing reagent provides the compounds of Formula I. Suitable oxidizing reagents include, for example, Dess-Martin periodinane or TEMPO and sodium hypochlorite.

The deuterated amino-alcohol-amides of Formula ii shown in Scheme 1 can be prepared by using known methods and, for example, as illustrated below in Scheme II.

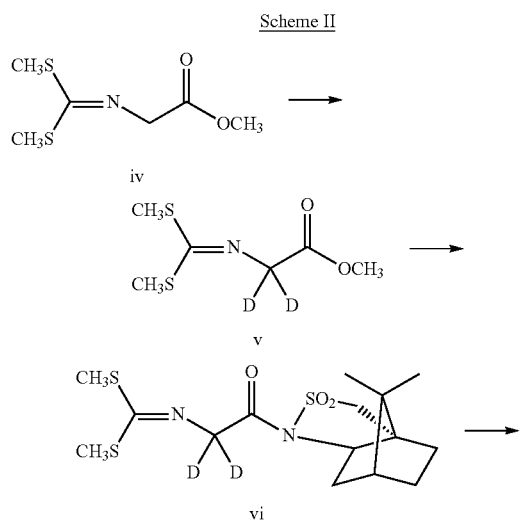

Scheme II

Referring to Scheme II, conversion of the glycine iminic ester iv to the deuterated sultam of Formula vii is conducted according to procedures previously described (Y. Elemes and U. Ragnarsson, *J. Chem. Soc., Perkin I,* 1996, 6, p. 537. Consecutive treatment of compounds of Formula vii with acid and base as previously described (L. Lankiewicz, et. al., *J. Chem. Soc., Perkin I,* 1994, 17, p. 2503 followed by treatment of the intermediate amino acid (not shown) with benzyloxycarbonyl chloride provides the protected deuterated amino acid viii. Reaction of viii with methoxymethylamine in the presence of the condensing reagent CDI provides the Weinreb amide of Formula ix. Reduction of vi with, for example, diisobutylaluminum hydride or lithium aluminum hydride provides the aldehyde x. Using procedures similar to those previously described (see, e.g., WO 02/18369), the aldehyde x is converted to the cyanohydrin xi and thence to the protected hydroxy-amino acid xii. The acid xii is converted to the protected amide xiii which is deprotected to provide the amino-amide ii.

Alternatively, the deuterated amino-amide ii depicted in Scheme I, wherein $R_2$ is H, may be prepared, e.g., as illustrated in Scheme III.

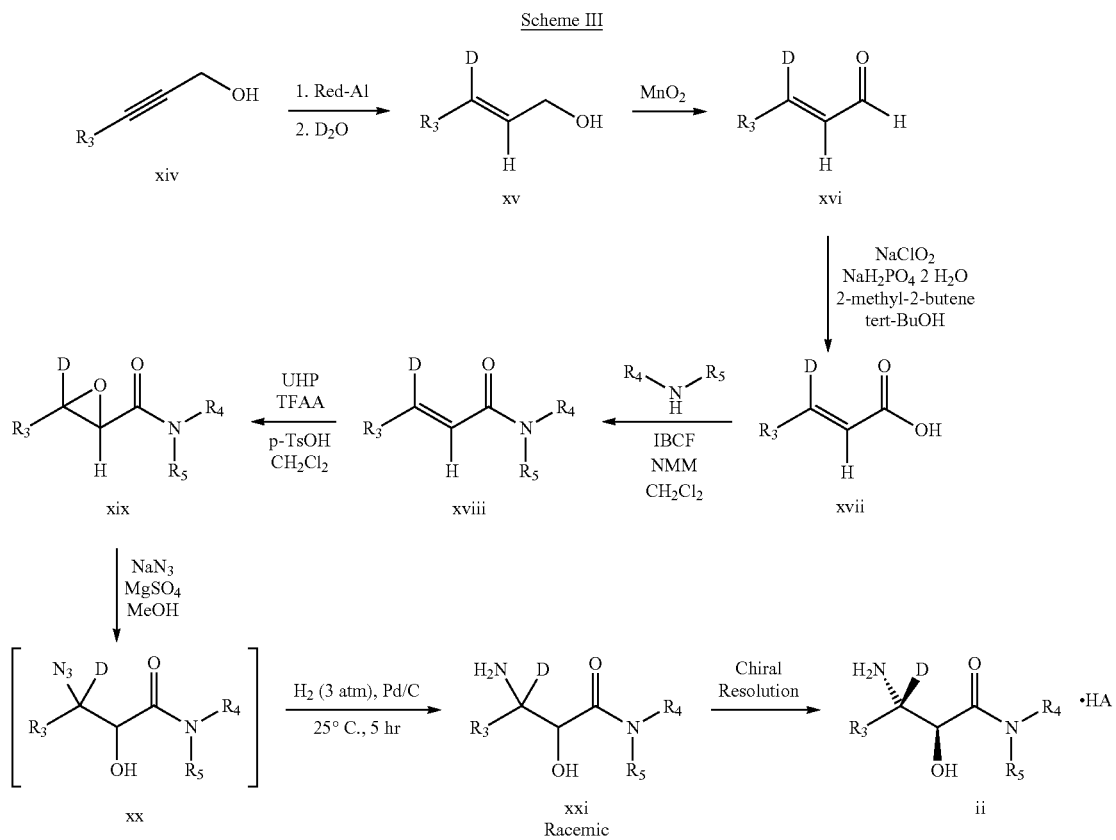

Referring to Scheme III, the propargyl alcohol xiv is reduced with sodium bis(2-methoxyethoxy)aluminumhydride, followed by quenching the reaction mixture with deuterium oxide to provide the deuterated allylic alcohol xv. Oxidation of xv with manganese dioxide provides the aldehyde xvi which is further oxidized to the acid xvii with sodium chlorite ($NaClO_2$) in the presence of sodium phosphate and 2-methyl-2-butene. Reaction of the acid xvii with isobutylchloroformate (ICBF) in the presence of N-methylmorpholine followed by reaction of the intermediate mixed anhydride with the amine $HNR_4R_5$ provides the amide xviii. Epoxidation of xviii to provide the epoxide xix may be achieved with urea hydrogen peroxide (UHP) in the presence of trifluoracetic acid and p-toluenesulfonic acid. Reaction of xix with sodium azide provides the intermediate azido compound xx which is subsequently reduced to the racemic-aminoalcohol xxi by catalytic hydrogenation in the presence of palladium on carbon. The racemic aminoalcohol xxi may be resolved using known methods such as chiral chromatography, preparation of optically active derivatives or the formation of salts with an optically active acid HA followed by crystallization from an organic solvent. Suitable optically active organic acids for preparing salts include, for example, L-tartaric acid, L-malic acid, (S)-mandelic acid, (1S)-(+)-10-camphorsulfonic acid, (−)2,2:4,6-di-O-isopropylidiene-2-keto-L-gulonic acid hydrate, N-acety-L-leucine, deoxycholic acid, (+)-O,O'-dibenzoyl-D-tartaric acid, O,O'-di-(4-toluoyl)-D-tartaric acid, S-(+)1,1-binaphtyl-2-2-phosphoric acid, L-lactic acid, D-Gluconic acid, lactobionic acid, dipivaloyl-L-tartaric acid, S-(+)-O-acetylmandelic acid and S-(−)-2-(phenylcarbamoyloxy)propionic acid. Examples of suitable organic solvents for recrystallization include dimethylacetamide, ethyl acetate and acetone.

The deuterated compounds thus obtained can be characterized by conventional analytical methods, e.g., NMR and Mass Spectroscope. NMR can be used to determine a compound's structure, while Mass Spectroscopy can be used to determine the amount of deuterium atom in the compound by comparison with its non-deuterated form.

The deuterated compounds of this invention are generally more stable and less inclined to epimerize than their non-deuterated analogs. Thus, they can be used in application where specific steric configuration in the compounds of this invention is desired. For instance, the deuterated compounds of formula (I) may be used to treat or prevent infection caused by HCV or other HCV protease-mediated condition, as they are capable of inhibiting HCV protease. Their inhibitory activity can be measured by traditional enzyme inhibition essays, some of which are described in the publications cited above. See, e.g., Perni, R. B. et al., Antimicrobial Agents and Chemotherapy, 2006 (march), 50 (3): 899-909.

Additionally, the deuterated compounds of formula (I) can be used as a biological tool to study the pharmacological properties of their non-deuterated analogs. Accordingly, these uses are also within the scope of this invention.

EXAMPLE 1

Preparation of (1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxo-3-deutero-hexan-3-yl)octahydrocyclopenta[c]pyrrole-1-carboxamide

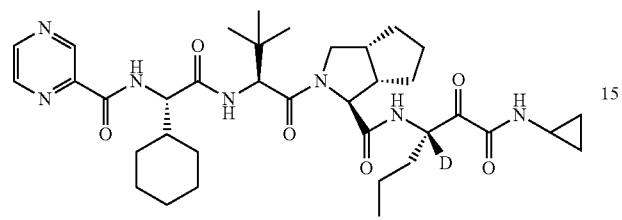

Step a: Preparation of

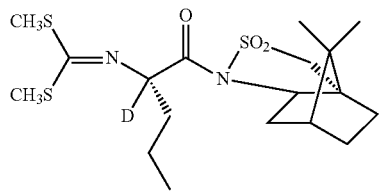

The deuterated sultam (i.e., compound vi shown in the scheme below) was prepared by known methods such as those described in Y. Elemes and U. Ragnarsson, *J. of Chem. Soc., Perkin* 1, 1996, 6, 537; W. Oppolzer, et. al., *Helv. Chim. Acta.*, 1994, 25: 2363, by using the corresponding unsubstituted sultam and propyl iodide.

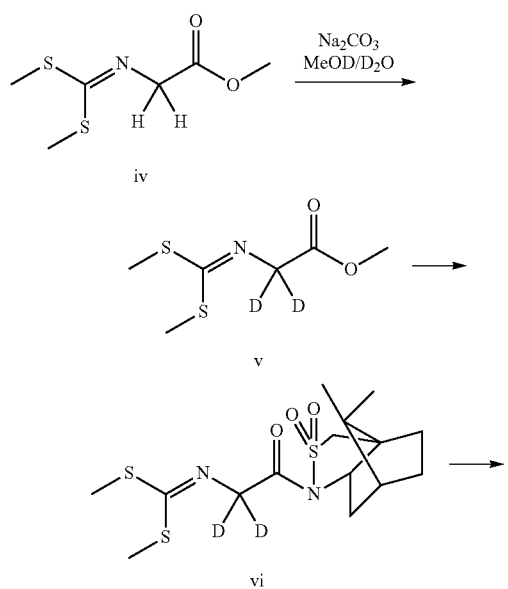

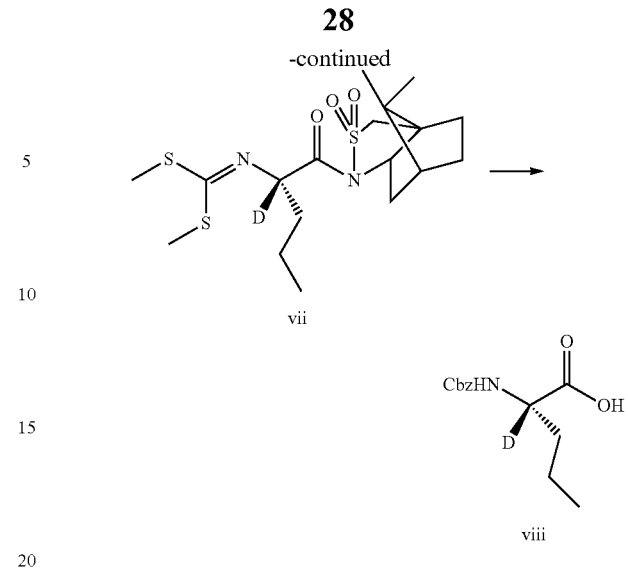

17.32 g of compound vi (45.8 mmol) and 229 mL of THF were then charged into a 500 mL round-bottomed-flask with a magnetic stir bar and $N_2$ inlet. The resulting solution was cooled to −78° C. and n-BuLi (31.5 mL of a 1.6 M solution in hexane, 50.3 mmol) was added with a syringe pump over an hour. The resulting yellow solution was aged for 30 minutes before a solution of HPMA (56 mL) and n-PrI (13.4 mL, 137 mmol) was added to it over 30 minutes. The mixture was allowed to warm to the room temperature over 8 hours and then cooled to −20° C. before $D_2O$ (50 mL) was added to the mixture. The reaction mixture was then extracted with EtOAc (400 mL) and the organic layer was dried over MgSO4 and concentrated to provide 61.3 g of the crude oil. Chromatography on 500 g of silica gel eluting with 2:1 heptane/EtOAc followed by concentration of the rich cut gave 20.35 g of a white solid. The white solid was then recrystallized from EtOH (210 mL) to give 15.39 g of compound vii as a white crystalline solid. The deuterium incorporation was 93% as determined by $^1H$ NMR.

Step b: Preparation of (S)-2-(benzyloxycarbonylamino)-2-deuteropentanoic acid, viii Compound vii (15.39 g, 32.1 mmol) from step a was charged into THF (100 mL) and 1N HCl (50 mL). The resulting emulsion was stirred overnight at the room temperature and then concentrated under vacuum to provide a thick oil. The oil was then dissolved in THF (100 mL), and to the solution was added water (25 mL) and LiOH (3.08 g, 128 mmol). This solution was stirred overnight again at the room temperature and then concentrated to remove THF. A hazy light yellow emulsion remained. This was diluted with water (25 mL) and extracted with $CH_2Cl_2$ (three times, 50 mL each). The aqueous phase was diluted with THF (200 mL) and cooled to 0° C. while stirring rapidly and CBZ—Cl (7.6 mL, 54 mmol) was added dropwise over 15 minutes. After stirring for an hour at 0° C., the THF solvent was removed in vacuo and the residue was acidified by addition of 1N HCl (50 mL). The solution was extracted with EtOAc (3 times, 100 mL each) and the organic phase was dried over $Na_2SO_4$ and concentrated to provide an oil. The residue was dissolved in EtOAc (25 mL) and heptane (150 mL), seeded and stirred overnight at the room temperature. The solids were collected on a frit, rinsed with heptane (30 mL) and air dried to give 5.65 g (70%) of compound viii shown in the scheme above. The deuterium incorporation was 93% as determined by $^1$H NMR.

Step c: Preparation of (S)-benzyl 1-(methoxy(methyl)amino)-1-oxo-2-deuteropentan-2-ylcarbamate

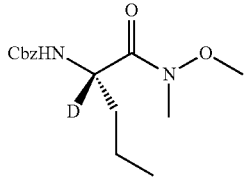

To a flask containing 1.0 g of (S)-2-(benzyloxycarbonylamino)-2-deuteropentanoic acid (3.97 mmol) in 20 mL of dichloromethane maintained at 0° C., was added 3.0 eq. of N-methylmorpholine (700 uL), 1.5 eq. of N,O-dimethylhydroxylamine hydrochloride (581 mg) and 1.5 eq. of EDCI (1.14 g). The reaction mixture was stirred overnight from 0° C. to the room temperature. The reaction mixture was then diluted in dichloromethane and washed with HCl (1N) and brine. The organic layer was dried over MgSO$_4$. The crude mixture was purified by flash chromatography (ethyl acetate 15-75% in hexanes) to afford 814 mg of pure amide (title compound). ES+=296.1, ES-=295.2. $^1$H NMR spectrum confirmed the structure.

Step d: Preparation of (S)-benzyl 1-oxo-2-deuteropentan-2-ylcarbamate

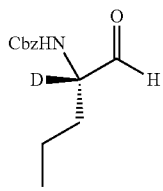

Using procedures described in WO 02/18369, the Cbz-protected amino acid of Step c is converted to the title compound. Specifically, into a flask containing 1.0 eq. of (S)-benzyl 1-(methoxy(methyl)amino)-1-oxo-2-deuteropentan-2-ylcarbamate (810 mg, 2.75 mmol) in 10 mL of dry THF maintained at 0° C. (in an ice bath) was added slowly 1.7 eq. of a solution of lithium borohydride (1.0M) (4.67 mL). After about 10 minutes, the ice bath was removed and the reaction continue for an hour. The reaction was quenched at 0° C. by adding 5 mL of a solution of KHSO$_4$ (10%). The solution was then diluted by the addition of 10 mL of HCl (1N). The mixture was stirred for 30 minutes, then extracted 3 times with dichloromethane. The organic phases were combined and washed with a solution of HCl (1 N), water and brine. The organic phase was then dried over MgSO$_4$ and the volatile evaporated. The aldehyde was used as is in the next step. ES+=237.1, ES-=235.2.

Step e: Preparation of benzyl (3S)-1-(cyclopropylamino)-2-hydroxy-1-oxo-3-deuterohexan-3-ylcarbamate

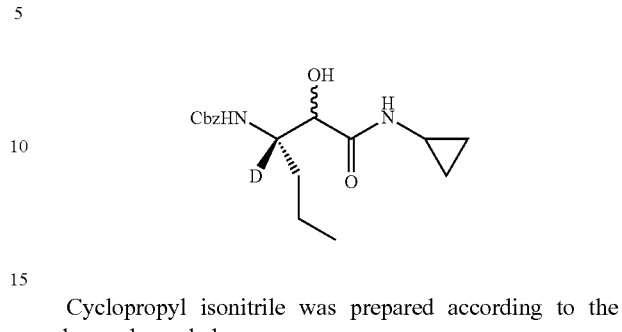

Cyclopropyl isonitrile was prepared according to the scheme shown below.

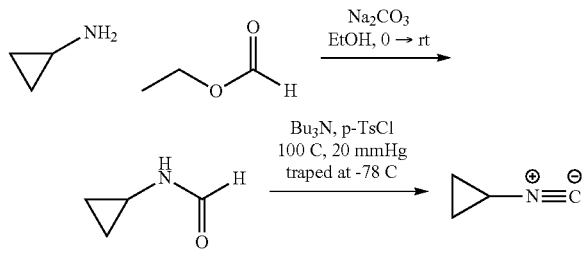

The cyclopropyl isonitrile was then coupled with the aldehyde product of Step d to give the title compound as described in J. E. Semple et al., Org. Lett., 2000, 2(18), p. 2769; Lumma W., *J. Org. Chem.*, 1981, 46, 3668". ES+=322.1.

Step f: Preparation of (3S)-3-amino-N-cyclopropyl-3-deutero-2-hydroxyhexanamide

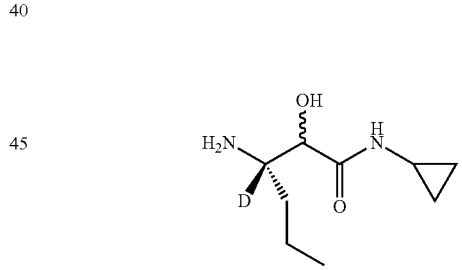

Hydrogenolysis of the Cbz compound of Step e was achieved by using a palladium on carbon catalyst in the presence of hydrogen to give the title compound. Shown in the following schemes are Steps c, d, e, and f.

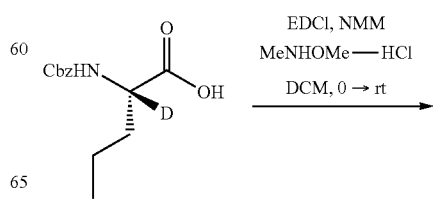

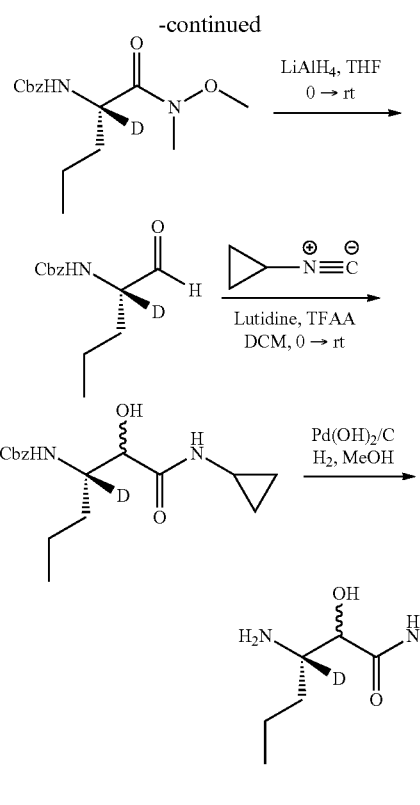

Step g: Preparation of (1S,3aR,6aS)-2-(S)-2-(S)-2-cyclohexyl-2-(pyrazine-2-carboxamido)acetamido)-3,3-dimethylbutanoyl)-N-((3S)-1-(cyclopropylamino)-3-deutero-2-hydroxy-1-oxohexan-3-yl)octahydrocyclopenta[c]pyrrole-1-carboxamide

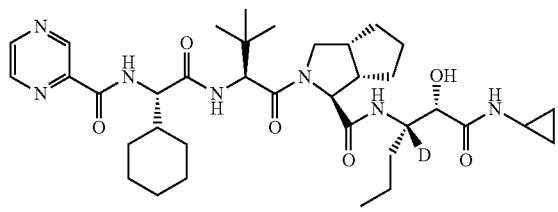

The title compound was prepared from the hydroxy-amino amide product of Step f by condensation with the appropriate acid in the presence of a coupling reagent such as, e.g., EDCI and HOSu. Specifically, in a flask containing 1.2 eq. of (1S,3aR,6aS)-2-((S)-2-((S)-2-cyclohexyl-2-(pyrazine-2-carboxamido)acetamido)-3,3-dimethylbutanoyl)octahydrocyclopenta[c]pyrrole-1-carboxylic acid (1.59 g) in 20 mL of DMF, was added 2.5 eq. of diisopropylamine (980 uL), 1.2 eq. N-hydroxybenzotriazole hydrate (411 mg) and 1.3 eq. of EDCI (558 mg). After 15 minutes of stirring at the room temperature, 1.0 eq. of (3S)-3-amino-N-cyclopropyl-3-deutero-2-hydroxyhexanamide hydrochloride (500 mg) was added to the mixture. After another 24 hours, the reaction mixture was diluted into 400 mL of ethyl acetate. The organic phase of the mixture was washed with HCl (1N), water, saturated sodium bicarbonate solution, brine, and then dried over MgSO₄. The crude product was purified by chromatography on silica (ethyl acetate 70-100% in Hexanes) to give 1.31 g of the tile compound as a white solid. ES+=683.6, ES-=682.2. The NMR ¹H confirmed the structure.

Step h: Preparation of (1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxo-3-deutero-hexan-3-yl)octahydrocyclopenta[c]pyrrole-1-carboxamide

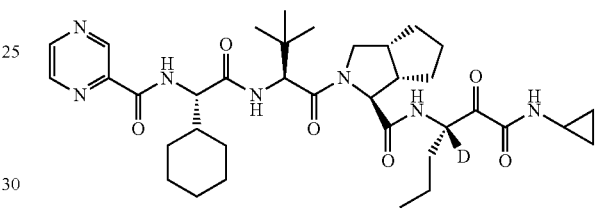

The title compound was prepared by oxidation of the product of Step g with a suitable oxidizing reagent such as Dess Martin periodinane or TEMPO and sodium hypochlorite. Specifically, in a flask containing 1.31 g of (1S,3aR,6aS)-2-((S)-2-((S)-2-cyclohexyl-2-(pyrazine-2-carboxamido)acetamido)-3,3-dimethylbutanoyl)-N-((3S)-1-(cyclopropylamino)-3-deutero-2-hydroxy-1-oxohexan-3-yl)octahydrocyclopenta[c]pyrrole-1-carboxamide in 40 mL of dichloromethane was added at room temperature 1.06 g of Dess Martin periodinane. After 2 hours of stirring, 50 mL of sodium bisulfite (1N) was added, and the mixture was stirred for 30 minutes. The 2 phases were separated, the organic was washed with water twice, brine and dried over Na2SO4. The crude product was purified by chromatography on silica (ethyl acetate 20-100% in Hexanes) to give 1.07 g of the title compound as a white solid. ES+=681.5, ES-=680.0. The ¹H NMR spectrum confirmed the structure.

Deuterium incorporation was determined by MS to be 93%. The diastereoisome ratio was determined by chiral HPLC normal phase and was higher than 99% d.e.

The following scheme shows the reactions of both Steps g and h.

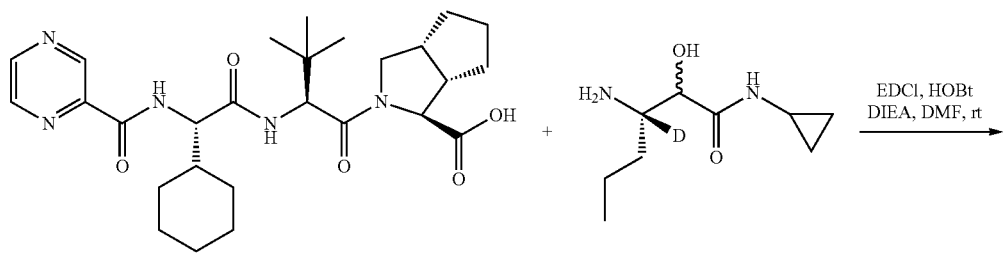

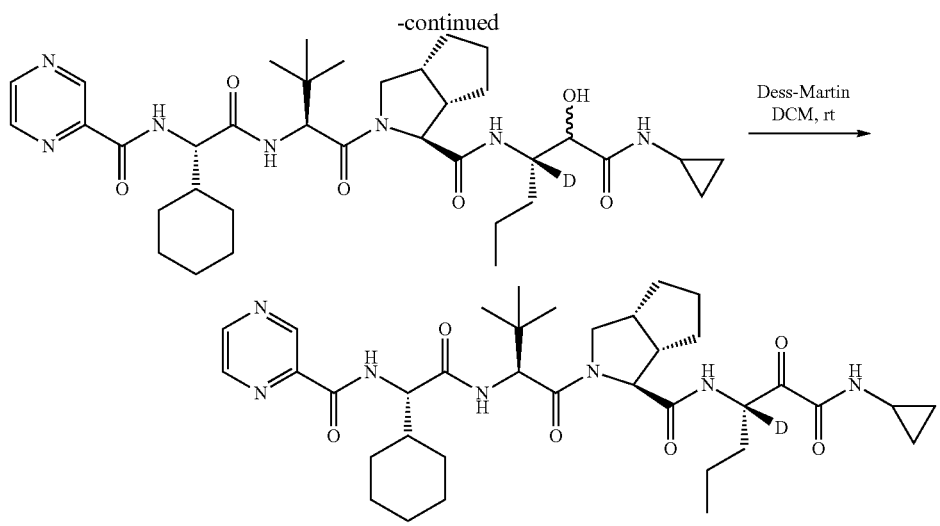
EXAMPLE 2
Preparation of (2S,3S)-3-amino-3-deutero-N-cyclopropyl-2-hydroxyhexanamide hydrochloride
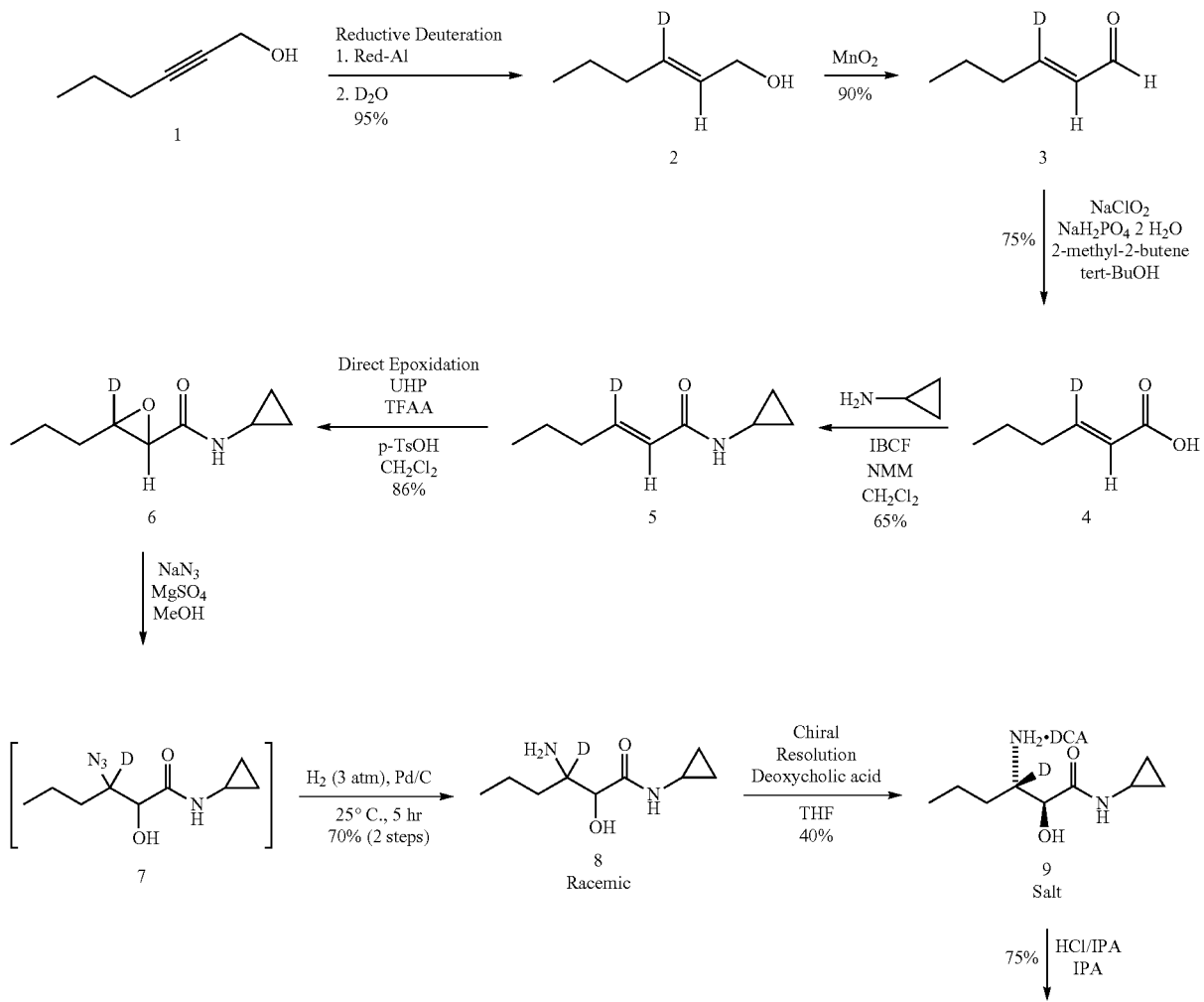

The scheme shown above illustrate the total synthesis of the title compound. Each step is described in detail as follows.

Step 1: Preparation of 3-deutero-(E)-hex-2-en-1-ol

To a three-neck 250 mL round bottom flask equipped with mechanical stirrer and reflux condenser was charged 2-hexyn-1-ol (10 g, 0.1 mole) and THF (100 mL, 10 vol). The resulting mixture was cooled to 0±5° C. and then Red-Al (65% in Toluene, 32 mL, 1.6 eq) was added slowly under a nitrogen atmosphere between 0° C. and 20° C. The resulting mixture was allowed to be warmed up to 25° C. and stirred for 5 hours. The reaction mixture was cooled down to −5±5° C. and $D_2O$ (8.2 g, 4 eq.) was added drop wise between 0° C. and 15° C. To the resulting mixture was charged IPAC (50 mL, 5 vol) and saturated $NH_4Cl$ solution (50 mL, 5 vol.). After stirring the mixture for 10 min, the white solid formed was filtered out. The organic layer from the filtrate was separated and the aqueous layer was extracted with IPAC (30 mL, 3 vol). The organic layers were combined and washed with water (30 mL, 3 vol) and dried over $MgSO_4$ and concentrated to afford 9.8 g of the product (compound 2) as a colorless oil. The crude product 2 was used for the next step without further purification.

$^1$H NMR (500 MHz, $CDCl_3$) δ 5.66 (t, 1H, J=5.0 Hz), 4.12 (d, 2H, J=5.0 Hz), 2.04 (t, 2H, J=5.0 Hz), 1.38~1.46 (m, 2H), 0.93 (t, 3H, J=5.0 Hz)

Step 2: Preparation of 3-deutero-(E)-hex-2-enal

To a three-neck 250 mL round bottom flask equipped with mechanical stirrer containing 3-deutero-2-hexenol (10 g, 0.1 mole) in $CH_2Cl_2$ (150 mL, 15 vol) was charged activated $MnO_2$ (87 g, 10 eq) at room temperature. After vigorous stirring for 1 hour, another portion of $MnO_2$ (16 g, 2 eq) was added and the shaking was continued for 4 hours. The reaction solution was filtered through a pad of celite. The solvent was removed in vacuo (25° C., 100 mmHg) to give 8.8 g of the crude aldehyde product (compound 3) as a pale yellowish oil. The crude product was used for the next step without further purification.

$^1$H NMR (500 MHz, $CDCl_3$) δ 9.54 (d, 1H, J=10.0 Hz), 6.14 (s, 1H), 2.34 (m, 2H), 1.55~1.60 (m, 2H), 1.00 (t, 3H, J=5.0 Hz)

Step 3: Preparation of 3-deutero-(E)-hex-2-enoic acid

To a three-neck 500 mL round bottom flask equipped with mechanical stirrer and reflux condenser was charged 3-deutero-2-Hexen-1-al (10 g, 0.1 mole), tert-BuOH (90 mL, 9 vol), and 2-methyl-2-butene (30 mL, 3 vol). The resulting solution was added with a freshly prepared aqueous $NaClO_2$ (27.4 g, 3 eq) and $NaH_2PO_4$ (62.9 g, 4 eq) in water (200 mL) over 30 minutes. The reaction mixture was stirred at room temperature for 2 hours. The reaction solution was cooled down to 0° C. and was added with saturated $Na_2SO_3$ aqueous solution until the reaction color becomes colorless. The stirring was stopped and the organic layer was separated and the aqueous layer was extracted with EtOAc (3 vol×3). The organic layers were combined and concentrated in vacuo until the total volume becomes 3 vol. The resulting solution was extracted with 1N NaOH (3 vol×3) and the remaining organic layer was discarded. The combined aqueous solution was acidified with 6 N HCl until the pH became 1.0. The solution was extracted with $CH_2Cl_2$ (3 vol×5). The combined organic layer were dried over $MgSO_4$ and concentrated to afford 8.7 g of the product (compound 4) as a white solid.

$^1$H NMR (500 MHz, CDCl3) δ 5.84 (s, 1H), 2.23 (t, 2H, J=5.0 Hz), 1.51~1.55 (m, 2H), 0.98 (t, 3H, J=5.0 Hz)

Step 4: Preparation of 3-deutero-(E)-N-cyclopropylhex-2-enamide

To a three-neck 250 mL round bottom flask equipped with mechanical stirrer and reflux condenser was charged 2-Hexenoic acid-3d (10 g, 0.09 mole), IBCF (13 g, 1.1 eq) in $CH_2Cl_2$ (100 mL, 10 vol). The resulting solution was cooled down to 0° C. and NMM (13.2 g, 1.5 eq) was added slowly by controlling the temperature between 0 and 20° C. Then, the mixture was allowed to be warmed up to room temperature and stirred for 1 hour. To the resulting solution was added cyclopropyl amine (5.9 g, 1.2 eq) and the solution was stirred for 2 hours. The reaction mixture was washed with 1N NaOH (3 vol×2), 1N HCl (3 vol×2), and brine solution (3 vol), and water (3 vol). The organic layer was dried over $MgSO_4$ and concentrated to afford the crude product as oil. The crude product was dissolved with heptane (5 vol) and cooled down to −78° C. with stirring. The precipitated solid was filter and dried to afford 8.7 g of the product (compound 5) as a white solid.

$^1$H NMR (500 MHz, DMSO) δ 7.92 (s, 1H), 5.78 (s, 1H), 2.66~2.68 (m, 1H), 2.08 (t, 2H, J=5.0 Hz), 1.38~1.42 (m, 2H), 0.87 (t, 3H, J=5.0 Hz), 0.63 (t, 2H, J=3.0 Hz), 0.40 (t, 2H, J=3.0 Hz)

Step 5: Preparation of 3-deutero-N-cyclopropyl-3-propyloxirane-2-carboxamide

To a three-neck 250 mL round bottom flask equipped with mechanical stirrer and containing (E)-N-cyclopropylhex-2-enamide-3d (i.e., product from Step 4) (10 g, 0.06 mole), urea hydrogen peroxide (25 g, 4 eq), and p-TsOH (12.3 g, 1 eq) in $CH_2Cl_2$ (100 mL, 10 vol) at 0° C. was added trifluoroacetic anhydride (40.9 g, 3 eq) in $CR_2Cl_2$ (50 mL, 5 vol) over 30 minutes. The reaction mixture was heated to 40±5° C. and stirred for 3 hours. After cooling to 0° C., the reaction mixture was quenched by adding 6 N NaOH (100 mL, 10 vol) slowly and stirring for 30 minutes. The organic layer was separated and washed with brine (5 vol) and water (5 vol). The washed organic layer was dried over $MgSO_4$ and solvent evaporated to afford 9.7 g of the epoxide product (i.e., compound 6) as pale yellow oil. The crude product was used for the next step without further purification.

$^1$H NMR (500 MHz, DMSO) δ 8.01 (s, 1H), 3.09 (s, 1H), 2.63-2.65 (m, 1H), 1.39~1.54 (m, 4H), 0.91 (t, 3H, J=5.0 Hz), 0.60 (t, 2H, J=3.0 Hz), 0.45 (t, 2H, J=3.0 Hz)

Step 6: Preparation of 3-azido-3-deutero-N-cyclopropyl-2-hydroxyhexanamide

To a three necked 250 mL round bottom flask equipped with mechanical stirrer and reflux condenser containing the epoxide-3d 6 (10 g, 0.06 mole) and anhydrous magnesium sulfate (14.1 g, 2.0 eq) in MeOH (100 mL, 10 vol) was added sodium azide (15.3 g, 4.0 eq) in one portion. The resulting mixture was heated to 65±5° C. and stirred for 5 hours. The reaction mixture was cooled to the room temperature and IPAC (100 mL, 10 vol) was added and the mixture was stirred for another 10 minutes. The mixture was filtered through a pad of Celite® to remove insoluble salts and the resulting clear solution was concentrated to 3 vol. To the resulting solution was added IPAC (170 mL, 17 vol) and the mixture was stirred for another 10 minutes. Again, the solution was filtered through a pad of Celite® to afford the product, the azide-3d (compound 7), as a clear solution in IPAC (about 200 mL), which was used for the next step without further purification.

$^1$H NMR (500 MHz, DMSO) δ 7.91 (s, 1H), 6.00 (d, 1H, J=5.0 Hz), 4.03 (d, 1H, J=5.0 Hz), 2.66~2.67 (m, 1H), 1.30~1.58 (m, 4H), 0.88 (t, 3H, J=5.0 Hz), 0.60 (t, 2H, J=3.0 Hz), 0.48 (t, 2H, J=3.0 Hz)

Step 7: Preparation of 3-amino-3-deutero-N-cyclopropyl-2-hydroxyhexanamide

To a 500 mL of autoclave hydrogenation reactor equipped with mechanical stirrer containing the azide-3d 7 (200 mL, 0.05 mole) in IPAC obtained in the previous step in a hydrogenation reactor was charged Pd/C (10% Pd, water 50%, 0.8 g). The solution was charged with nitrogen (1.0 atm) and released three times and then charged with hydrogen (3.0 atm) and released three times. The resulting solution was charged with hydrogen (3 atm) and stirred for 5 hours. After releasing the hydrogen gas, the solution was purged with nitrogen for 5 minutes. To the resulting solution was added MeOH (30 ml, 3 vol) and the reaction mixture was heated to 50±5° C. The reaction mixture was filtered through a pad of celite to afford a clear solution. The product was isolated by concentrating the solution at 20±5° C. until 3 vol of the solution remained. The solid was collected by filtration, washed (IPAC, 3 vol), and dried to give 7.7 g of the title compound (compound 8) as a white crystalline solid.

$^1$H NMR (500 MHz, DMSO) δ 7.70 (s, 1H), 5.31 (s, 2H), 3.68 (s, 1H), 2.64~2.66 (m, 1H), 1.10~1.50 (m, 4H), 0.82 (t, 3H, J=5.0 Hz), 0.59 (t, 3H, J=3.0 Hz), 0.45 (t, 3H, J=3.0 Hz)

Step 8: Preparation of (2S,3S)-3-amino-3-deutero-N-cyclopropyl-2-hydroxyhexanamide deoxycholate Deoxycholic acid (15.7 g, 0.75 eq.) was charged to a three-neck 250 mL round bottom flask equipped with mechanical stirrer and containing the racemic (2S,3S)-3-amino-3-deutero-N-cyclopropyl-2-hydroxyhexanamide of step 7 (10 g, 0.05 mole) in THF (100 mL, 10 v). The reaction mixture was heated to 65±5° C. and stirred for 1 hour. The resulting homogeneous mixture was cooled to 23±2° C. over 1 hour, and left at the same temperature range for 1 hour. The precipitated solids were collected by filtration, washed with THF (50 mL, 5 vol), and dried to give 12.4 g of the salt compound (compound 9) as a white solid. The product has an enantiomeric ratio (ER) of 2:98.

Step 9: Preparation of (2S,3S)-3-amino-3-deutero-N-cyclopropyl-2-hydroxyhexanamide hydrochloride To a three-neck 250 mL round bottom flask equipped with mechanical stirrer was charged the dihydrocholate salt (from step 8) and 2-propanol (62 mL, 5 vol). The solution was heated to 75±5° C. and 5 to 6 N HCl solution in IPA (12 mL, 3 eq.) was added slowly with vigorous stirring. The resulting solution was stirred at the same temperature for 1 hour and then cooled down to 23±2° C. The reaction mixture was maintained at the same temperature for 1 hour. The precipitated solids were collected by filtration, washed with 2-propanol (36 mL, 3 vol), dried to give 3.0 g of the title compound (enantiomeric ratio=0:100) as a white solid. The deuterium incorporation was higher than 99% as determined by MS and $^1$H NMR.

$^1$H NMR (500 MHz, DMSO) δ 8.07 (s, 1H), 7.97 (s, 3H), 6.25 (d, 1H, J=5.0 Hz), 4.16 (d, 1H, J=5.0 Hz), 2.67-2.70 (m, 1H), 1.33~1.46 (m, 4H), 0.84 (t, 3H, J=5.0 Hz), 0.61 (t, 3H, J=3.0 Hz), 0.53 (t, 3H, J=3.0 Hz).

EXAMPLE 3

Assay for Measuring Epimerization Rate

The deuterated compounds of this invention undergo slow epimerization as follows:

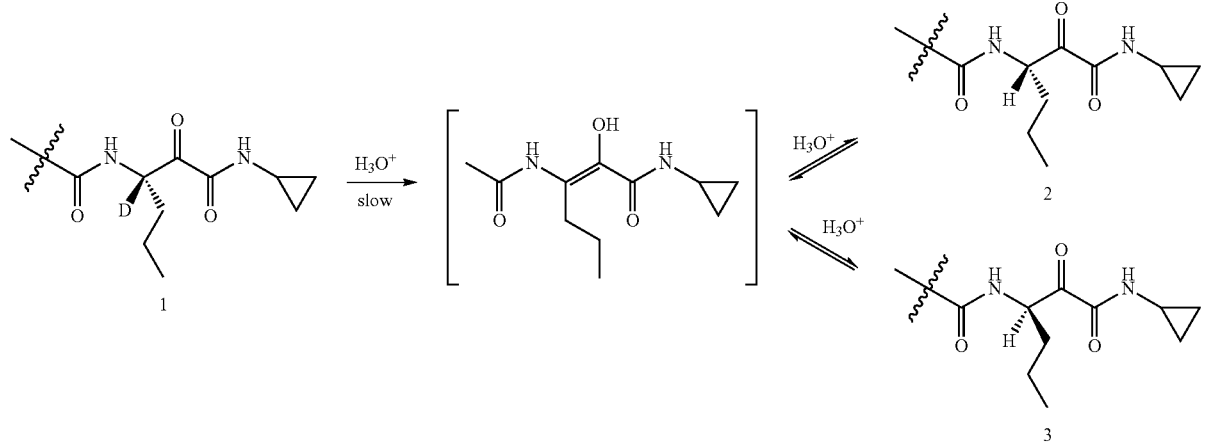

The epimerization rate was measured according to the following assay. Specifically, 100 μL medium (buffer, rat plasma, dog plasma, or human plasma) was added into a 96-well deep plate. To the plasma was then added 10 μL acetonitrile solution containing a test compound (1S,3aR, 6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxo-3-deutero-hexan-3-yl) octahydrocyclopenta[c]pyrrole-1-carboxamide (at 1 uM or 10 uM) and 1200 μL ethyl acetate into the 96 deep-well plate (2 mL) by using a TomTec liquid handling workstation (Hamden, Conn., USA). The plate was then covered tightly and shaken with a vortex for 20 minutes before it was centrifuged at 3000 rpm for 10 minutes. After centrifuge, 900 μL of the supernatant was transferred to a new V-shape 96 deep-well plate using TomTec, and then dried under nitrogen gas (flow rate of 60 L/min) at 25° C. for about 30 minutes. The residue was reconstituted with 100 μL ethyl acetate, and the solution was again transferred into the glass inserts in the 96-well plate. 20 uL of the reconstituted solution was injected into LC-MS/MS to determine the amount of the epimers. The LC-MS/MS spectrometer used a ChiralPak AD Column (4.6× 150 mm, 10 μm), a mixture of isopropanol and n-heptane (10:90, 50:50, or 90:10) as the mobile phase, and isopropanol as the washing solvent. Also used in the MS spectrometer was a deuterated analog of the test compound containing 11 deuterium atoms in the cyclohexyl group ($C_{36}H_{42}D_{11}N_7O_6$, MW 690.47).

The test compound had a mass (M+H, m/z) of 681.36, while its non-deuterated analogs (with the same or different chiral configurations at the deuterated carbon center) had a mass (M+H, m/z) of 680.36. Their LC-MS/MS spectra showed a fragment of 323.30 (with deuterium) and 322.30 (non-deuterated).

At both concentrations (1 μM and 10 uM) and in the same medium (i.e., a buffer, rate plasma, dog plasma, and human plasma), the test deuterated compound of formula (I) showed a slower epimerization rate than its non-deuterated form buffer, rat plasma, and dog plasma; and a much slower epimerization rate in human plasma. For instance, in human plasma and at 1 uM or 10 uM, the deuterated compound epimerized for about 30% in 180 minutes, whereas the non-deuterated form epimerized for almost 40%. In addition, in human plasma, the deuterated compound epimerized at a linear rate for 180 minutes, while the non-deuterated form showed an exponential rate of epimerization in the first 60 minutes before it leveled off.

EXAMPLE 4

Assay for Determining $IC_{50}$ in HCV Replicon Cells (1S,3aR,6aS)-2-((S)-2-((S)-2-cyclohexyl-2-(pyrazine-2-carboxamido)acetamido)-3,3-dimethylbutanoyl)-N—((S)-1-(cyclopropylamino)-1,2-dioxo-3-deutero-hexan-3-yl)octahydrocyclopenta[c]pyrrole-1-carboxamide and (5S,8S)-3-(5-chloro-2,4-dimethoxyphenyl)-7-((S)-2-(2-cyclohexylacetamido)-3,3-dimethylbutanoyl)-N—((S)-1-(cyclopropylamino)-1,2-dioxo-3-deuterohexan-3-yl)-1-oxa-2,7-diazaspiro[4.4]non-2-ene-8-carboxamide were used in this assay as described in Lin, C. et al., *J. Biol. Chem.*, 2004, 279: 17508-17514; Lin, K. et al., *Antimicrob. Agents Chemother.*, 2004, 48:4784-4792.

Huh-7 cells harboring an autonomously replicating, subgenomic HCV replicon of the Con1 strain were maintained in Dulbecco's modified Eagle's medium (DMEM), 10% heat-inactivated fetal bovine serum (FBS), 2 mM L-glutamine, and nonessential amino acids (JRH Biosciences, Lenexa, Kans.), plus 0.25 mg/ml G418 (Invitrogen, Carlsbad, Calif.). The subgenomic HCV replicon also encodes a neomycin phosphotransferase, which allows selective growth of HCV replicon-containing Huh-7 cells over HCV replicon-negative Huh-7 cells in the presence of G418. The concentrations of the test compound at which the HCV RNA level in the replicon cells is reduced by 50% ($IC_{50}$) or by 90% ($IC_{90}$) or the cell viability is reduced by 50% ($CC_{50}$), were determined in HCV Con1 subgenomic replicon cells (19) using 4-parameter curve fitting (SoftMax Pro). The replicon cells were incubated with the test compound diluted in DMEM containing 2% FBS and 0.5% DMSO (without G418) at 37° C. Total cellular RNA was extracted using an RNeasy-96 kit (QIAGEN, Valencia, Calif.), and the copy number of the HCV RNA was determined in a quantitative, real-time, multiplex reverse transcription-PCR (QRT-PCR, or Taqman) assay. The cytotoxicity of compounds in the HCV replicon cells was measured under the same experimental settings using the tetrazolium-based cell viability assay.

The results show that both test compounds have a Ki of less than 50 nM, and an $IC_{50}$ (over 5 days) of less than 10.0 uM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A process for preparing a salt of an optically enriched compound of Formula 1

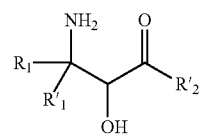

wherein:
$R_1$ is independently H, optionally substituted aliphatic, optionally substituted cycloaliphatic, optionally substituted arylaliphatic, optionally substituted heteroaliphatic or optionally substituted heteroarylaliphatic;
$R'_1$ is deuterium such that the deuterium enrichment is at least 50%;
$R'_2$ is —$NHR_2$ or —OE;
$R_2$ is H, optionally substituted aliphatic, optionally substituted cycloaliphatic, optionally substituted arylaliphatic, optionally substituted heteroaliphatic or optionally substituted heteroarylaliphatic; and
E is $C_{1-6}$ alkyl or benzyl;
comprising the steps of:
a) forming a salt of a racemic compound of Formula 1, and
b) crystallizing said salt to give a compound of greater than 55% enantiomeric excess.

2. The process of claim 1, wherein $R_1$ is $C_{1-6}$ alkyl, and $R'_2$ is —$NHR_2$ wherein $R_2$ is a $C_{1-6}$ alkyl or $_{C1-6}$ cycloalkyl.

3. The process of claim 2, wherein $R_1$ is propyl and $R_2$ is cyclopropyl.

4. The process of claim 1, further comprising aminating a compound of Formula ii

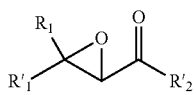

with an aminating reagent to provide a compound of Formula iii

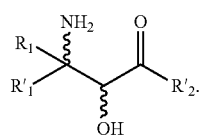

5. The process of claim 4, wherein the aminating reagent is an azide salt and the intermediate azido compound is reduced by hydrogenation.

6. The process of claim 4, further comprising oxidizing an unsaturated compound of Formula i

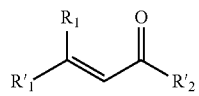

wherein $R'_2$ is —$NHR_2$ or —OE, wherein E is $C_{1-5}$ alkyl or benzyl, with an oxidizing reagent to provide a compound of Formula ii

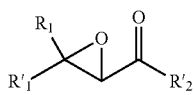

7. The process of claim 6, wherein the oxidizing reagent comprises t-butyl hydroperoxide.

8. The process of claim 7, wherein the oxidizing reagent further comprises a chiral reagent.

9. The process of claim 6, wherein the oxidizing reagent is a mixture of samarium (III) isopropoxide, triphenyl arsine oxide, S—(-)1,1'-bi-2-naphthol and 4 Å molecular sieves.

10. The process of claim 6, wherein the oxidizing reagent comprises urea-hydrogen peroxide in the presence of trifluoroacetic anhydride.

11. The process of claim 10, wherein $R'_2$ is —OE.

12. The process of claim 10, wherein $R'_2$ is —$NHR_2$.

13. The process of claim 6, further comprising hydrolyzing the compound of Formula ii to give an acid and then converting the acid to an amide compound of Formula ii wherein $R'_2$ is —$NHR_2$.

14. The process of claim 6, further comprising oxidizing a compound of Formula iv

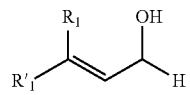

to give the compound of Formula ii.

15. The process of 14, wherein the oxidation is conducted by using manganese dioxide.

16. The process of 14, further comprising reducing a compound of Formula v

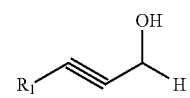

to give the compound of Formula iv.

17. The process of 16, wherein the compound is reduced with Red-Al® and then quenched with deuterium oxide.

18. A process for preparing a salt of an optically enriched compound of Formula 1

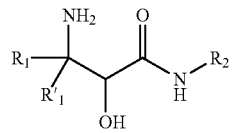

wherein:
$R_1$ is H, optionally substituted aliphatic, optionally substituted cycloaliphatic, optionally substituted arylaliphatic, optionally substituted heteroaliphatic or optionally substituted heteroarylaliphatic;
$R'_1$ is deuterium,
$R_2$ is H, optionally substituted aliphatic, optionally substituted cycloaliphatic, optionally substituted arylaliphatic, optionally substituted heteroaliphatic or optionally substituted heteroarylaliphatic; and
the compound of Formula 1 has an enantiomeric excess of greater than 55%, comprising the steps of:
a) oxidation of an unsaturated compound of Formula i

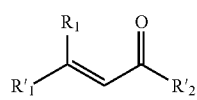

to provide a compound of formula ii

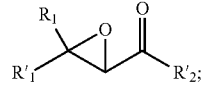

b) reacting a compound of Formula ii with an aminating reagent to provide a racemic compound of Formula iii

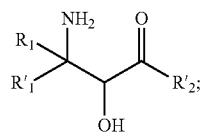
c) forming a salt of a compound of Formula iii with an optically active organic acid;
d) crystallizing said salt to give a compound of greater than 55% enantiomeric excess.
19. The process of claim 18, wherein the compound of Formula 1 is (2S,3S)-3-amino-3-deutero-N-cyclopropyl-2-hydroxyhexanamide.
20. The process of claim 19, wherein the organic acid is L-tartaric acid or deoxycholic acid.
* * * * *